(12) United States Patent
Fischer

(10) Patent No.: US 12,740,836 B2
(45) Date of Patent: Sep. 22, 2026

(54) ROBOTIC SURGICAL SYSTEM WITH INSTRUMENT BAILOUT AND LOCKOUT FEATURES

(71) Applicant: Cilag GmbH International, Zug (CH)

(72) Inventor: Austin M. Fischer, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 928 days.

(21) Appl. No.: 18/092,571

(22) Filed: Jan. 3, 2023

(65) Prior Publication Data

US 2024/0216082 A1 Jul. 4, 2024

(51) Int. Cl.

*A61B 34/30* (2016.01)
*A61B 17/295* (2006.01)
*A61B 17/32* (2006.01)
*A61B 34/00* (2016.01)

(52) U.S. Cl.

CPC ............ *A61B 34/30* (2016.02); *A61B 17/295* (2013.01); *A61B 34/70* (2016.02); *A61B 2017/320095* (2017.08); *A61B 2034/305* (2016.02)

(58) Field of Classification Search

CPC ......... A61B 34/71; A61B 34/30; A61B 17/29; A61B 18/1445

See application file for complete search history.

(56) References Cited

U.S. PATENT DOCUMENTS 7,354,440 B2 4/2008 Truckai et al.
7,381,209 B2 6/2008 Truckai et al.
8,663,220 B2 3/2014 Wiener et al.
9,949,785 B2 4/2018 Price et al.
2009/0024141 A1* 1/2009 Stahler .................. A61B 34/71 606/130
2022/0249182 A1* 8/2022 Definis .................. A61B 17/29

* cited by examiner

*Primary Examiner* — Ronald Hupczey, Jr.
(74) *Attorney, Agent, or Firm* — FBT Gibbons LLP

(57) ABSTRACT

An apparatus includes an end effector, a shaft assembly, an instrument base, and a bailout assembly. The instrument base includes at least one input assembly capable of engaging an output assembly of a robotic arm. The bailout assembly includes an actuating body and a driving assembly. The actuating body is capable of actuating relative to instrument base from a pre-bailout position, an engaged position, and a bailout position. The driving assembly is capable of actuating from a first position toward a second position to drive the output assembly of the robotic arm out of engagement with the at least one input assembly of the instrument base in response to the actuating body actuating from the engaged position into the bailout position. The driving assembly remains in the first position while the actuating body is in the pre-bailout position.

20 Claims, 31 Drawing Sheets

230
214
240
232
252
258
256
278
274
276
254
272
271
242
246
270
260
234
250
220
218
216

ROBOTIC SURGICAL SYSTEM WITH INSTRUMENT BAILOUT AND LOCKOUT FEATURES

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically assisted surgery. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein; and U.S. Pat. No. 8,663,220, entitled "Ultrasonic Surgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
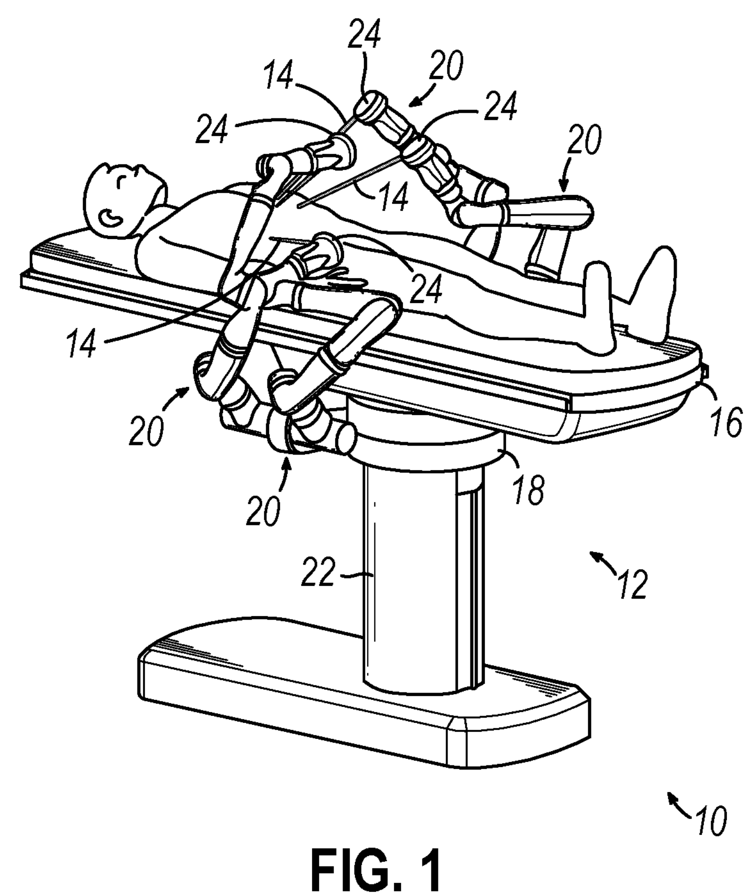
FIG. 1 depicts a perspective view of a first example of a table-based robotic system configured for a laparoscopic procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms “proximal” and “distal” are defined herein relative to a human or robotic operator of the surgical instrument. The term “proximal” refers the position of an element closer to the human or robotic operator of the surgical instrument and further away from the surgical end effector of the surgical instrument. The term “distal” refers to the position of an element closer to the surgical end effector of the surgical instrument and further away from the human or robotic operator of the surgical instrument. It will be further appreciated that, for convenience and clarity, spatial terms such as “front,” “rear,” “clockwise,” “counterclockwise,” “longitudinal,” and “transverse” also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

In addition to performing the breadth of procedures, the robotically-enabled medical system may provide additional benefits, such as enhanced imaging and guidance to assist the medical professional. Additionally, the robotically-enabled medical system may provide the medical professional with the ability to perform the procedure from an ergonomic position without the need for awkward arm motions and positions. Still further, the robotically-enabled medical system may provide the medical professional with the ability to perform the procedure with improved ease of use such that one or more of the instruments of the robotically-enabled medical system may be controlled by a single operator.

I. Illustrative Robotically-Enabled Medical System

FIG. 1 shows an illustrative robotically-enabled medical system, including a first example of a table-based robotic system (10). Table-based robotic system (10) of the present example includes a table system (12) operatively connected to an instrument for a diagnostic and/or therapeutic procedure in the course of treating a patient. Such procedures may include, but are not limited, to bronchoscopy, ureteroscopy, a vascular procedure, and a laparoscopic procedure. To this end, the instrument illustrated in the present example is an RF energy enabled surgical instrument (14) configured for a laparoscopic procedure, although it will be appreciated that any instrument for treating a patient may be similarly used. At least part of table-based robotic system (10) may be constructed and operable in accordance with at least some of the teachings of any of the various patents, patent application publications, and patent applications that are cited herein. As described therein and as will be described in greater detail below, RF energy surgical instrument (14) is operable to sever tissue and/or apply RF therapeutic energy to tissue. While one or more examples incorporates various RF electrosurgical energy features, such as RF energy surgical instrument (14), the invention is not intended to be unnecessarily limited to the RF features described herein.

A. First Illustrative Table-Based Robotic System

With respect to FIG. 1, table-based robotic system (10) includes table system (12) having a platform, such as a table (16), with a plurality of carriages (18) which may also be referred to herein as "arm supports," respectively supporting the deployment of a plurality of robotic arms (20). Table-based robotic system (10) further includes a support structure, such as a column (22), for supporting table (16) over the floor. Table (16) may also be configured to tilt to a desired angle during use, such as during laparoscopic procedures. Each robotic arm (20) includes an instrument driver (24) configured to removably connect to and manipulate RF energy surgical instrument (14) for use. In alternative examples, instrument drivers (24) may be collectively positioned in a linear arrangement to support the instrument extending therebetween along a "virtual rail" that may be repositioned in space by manipulating the one or more robotic arms (20) into one or more angles and/or positions. In practice, a C-arm (not shown) may be positioned over the patient for providing fluoroscopic imaging.

In the present example, column (22) includes carriages (18) arranged in a ring-shaped form to respectively support one or more robotic arms (20) for use. Carriages (18) may translate along column (22) and/or rotate about column (22) as driven by a mechanical motor (not shown) positioned within column (22) in order to provide robotic arms (20) with access to multiples sides of table (16), such as, for example, both sides of the patient. Rotation and translation of carriages (18) allows for alignment of instruments, such as RF energy surgical instrument (14) into different access points on the patient. In alternative examples, such as those discussed below in greater detail, table-based robotic system (10) may include a patient table or bed with adjustable arm supports including a bar (26) (see FIG. 2) extending alongside. One or more robotic arms (20) (e.g., via a shoulder with an elbow joint) may be attached to carriages (18), which are vertically adjustable so as to be stowed compactly beneath the patient table or bed, and subsequently raised during use.

Table-based robotic system (10) may also include a tower (not shown) that divides the functionality of table-based robotic system (10) between table (16) and the tower to reduce the form factor and bulk of table (16). To this end, the tower may provide a variety of support functionalities to table (16), such as processing, computing, and control capabilities, power, fluidics, and/or optical and sensor processing. The tower may also be movable so as to be positioned away from the patient to improve medical professional access and de-clutter the operating room. The tower may also include a master controller or console that provides both a user interface for operator input, such as keyboard and/or pendant, as well as a display screen, including a touchscreen, for pre-operative and intra-operative information, including, but not limited to, real-time imaging, navigation, and tracking information. In one example, the tower may include gas tanks to be used for insufflation.

B. Second Illustrative Table-Based Robotic System

Figure 2:
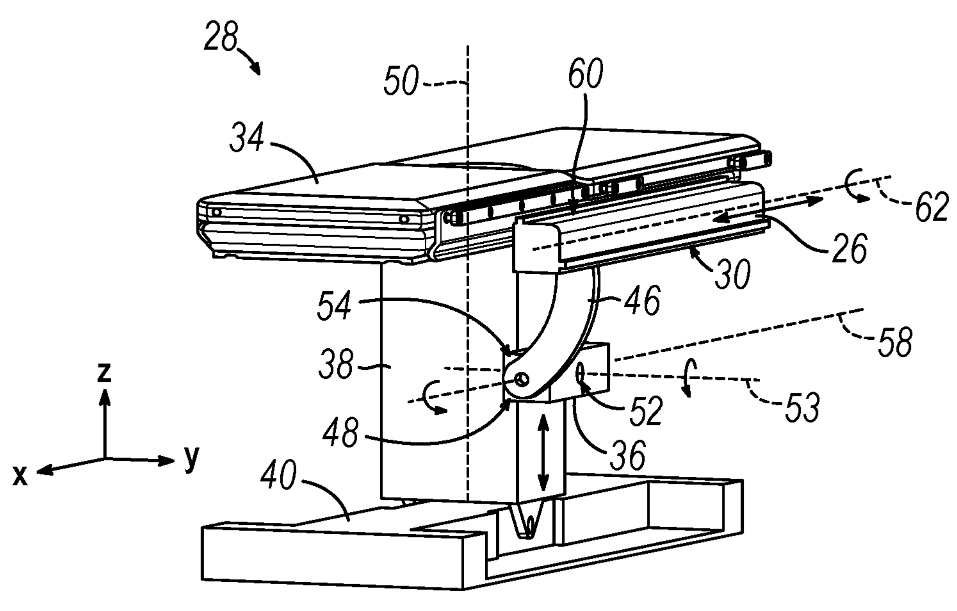
FIG. 2 depicts a perspective view of a second example of a table-based robotic system.
Figure 3:
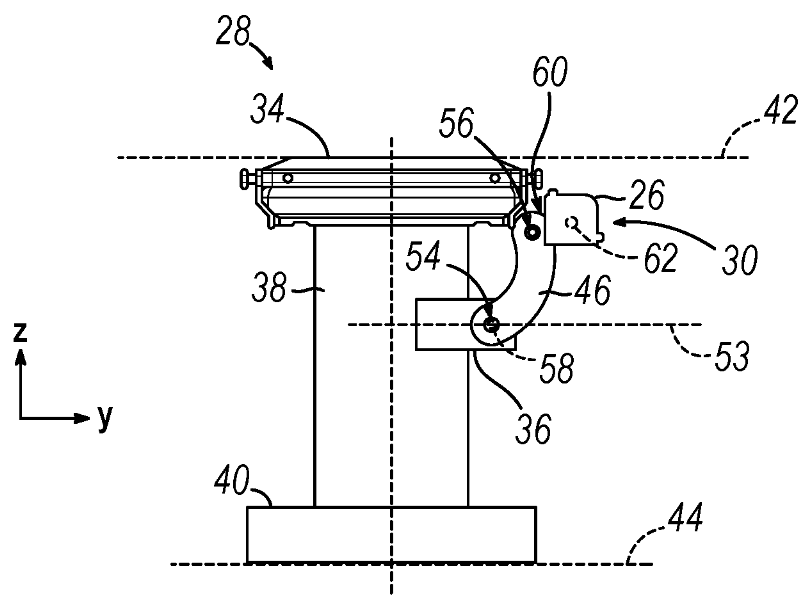
FIG. 3 depicts an end elevational view of the table-based robotic system of FIG. 2.
Figure 4:
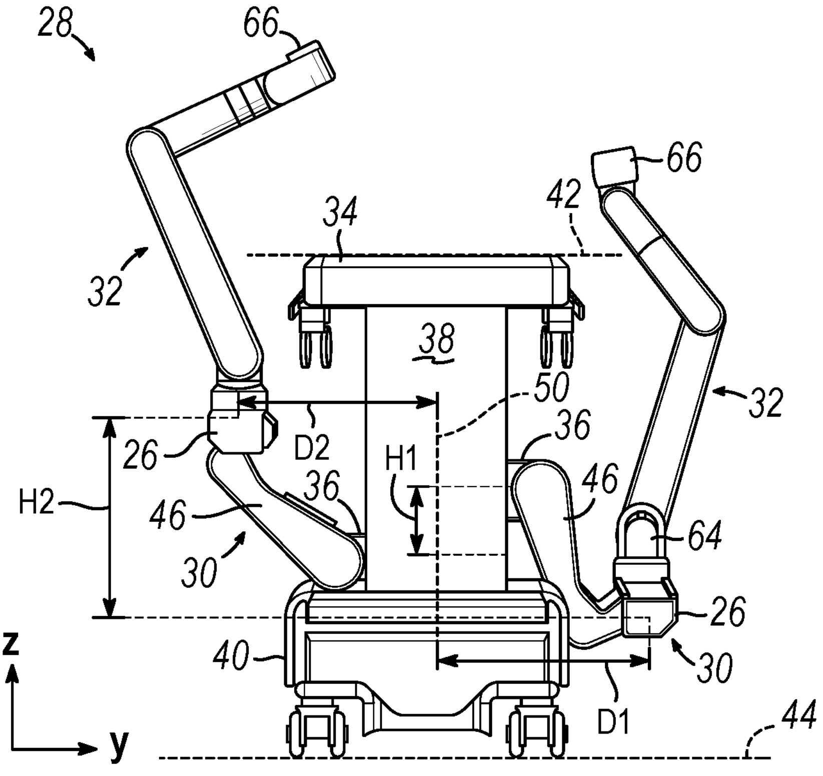
FIG. 4 depicts the end elevational view of the table-based robotic system of FIG. 3 including a pair of illustrative robotic arms.

As discussed briefly above, a second illustrative table-based robotic system (28) includes one or more adjustable arm supports (30) including bars (26) configured to support one or more robotic arms (32) relative to a table (34) as shown in FIGS. 2-4. In the present example, a single and a pair of adjustable arm supports (30) are shown, though additional arm supports (30) may be provided about table (34). Adjustable arm support (30) is configured to selectively move relative to table (34) so as to alter the position of adjustable arm support (30) and/or any robotic arms (32) mounted thereto relative to table (34) as desired. Such adjustable arm supports (30) provide high versatility to table-based robotic system (28), including the ability to easily stow one or more adjustable arm supports (30) with robotic arms (32) beneath table (34).

Each adjustable arm support (30) provides several degrees of freedom, including lift, lateral translation, tilt, etc. In the present example shown in FIGS. 2-4, arm support (30) is configured with four degrees of freedom, which are illustrated with arrows. A first degree of freedom allows adjustable arm support (30) to move in the z-direction ("Z-lift"). For example, adjustable arm support (30) includes a vertical carriage (36) configured to move up or down along or relative to a column (38) and a base (40) supporting table (34). A second degree of freedom allows adjustable arm support (30) to tilt about an axis extending in the y-direction. For example, adjustable arm support (30) includes a rotary joint, which allows adjustable arm support (30) to align the bed in a Trendelenburg position. A third degree of freedom allows adjustable arm support (30) to "pivot up" about an axis extending in the x-direction, which may be useful to adjust a distance between a side of table (34) and adjustable arm support (30). A fourth degree of freedom allows translation of adjustable arm support (30) along a longitudinal length of table (34), which extends along the x-direction. Base (40) and column (38) support table (34) relative to a support surface, which is shown along a support axis (42) above a floor axis (44) and in the present example. While the present example shows adjustable arm support (30) mounted to column (38), arm support (30) may alternatively be mounted to table (34) or base (40).

As shown in the present example, adjustable arm support (30) includes vertical carriage (36), a bar connector (46), and bar (26). To this end, vertical carriage (36) attaches to column (38) by a first joint (48), which allows vertical carriage (36) to move relative to column (38) (e.g., such as up and down a first, vertical axis (50) extending in the z-direction). First joint (48) provides the first degree of freedom ("Z-lift") to adjustable arm support (30). Adjustable arm support (30) further includes a second joint (52), which provides the second degree of freedom (tilt) for adjustable arm support (30) to pivot about a second axis (53) extending in the y-direction. Adjustable arm support (30) also includes a third joint (54), which provides the third degree of freedom ("pivot up") for adjustable arm support (30) about a third axis (58) extending in the x-direction. Furthermore, an additional joint (56) mechanically constrains third joint (54) to maintain a desired orientation of bar (26) as bar connector (46) rotates about third axis (58). Adjustable arm support (30) includes a fourth joint (60) to provide a fourth degree of freedom (translation) for adjustable arm support (30) along a fourth axis (62) extending in the x-direction.

With respect to FIG. 4, table-based robotic system (28) is shown with two adjustable arm supports (30) mounted on opposite sides of table (34). A first robotic arm (32) is attached to one such bar (26) of first adjustable arm support (30). First robotic arm (32) includes a base (64) attached to bar (26). Similarly, second robotic arm (32) includes base (64) attached to other bar (26). Distal ends of first and second robotic arms (32) respectively include instrument drivers (66), which are configured to attach to one or more instruments such as those discussed below in greater detail.

In one example, one or more robotic arms (32) has seven or more degrees of freedom. In another example, one or more robotic arms (32) has eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base (64) (1-degree of freedom including translation). In one example, the insertion degree of freedom is provided by robotic arm (32), while in another example, such as RF energy surgical instrument (14) (see FIG. 6A), the instrument includes an instrument-based insertion architecture.

Figure 5:
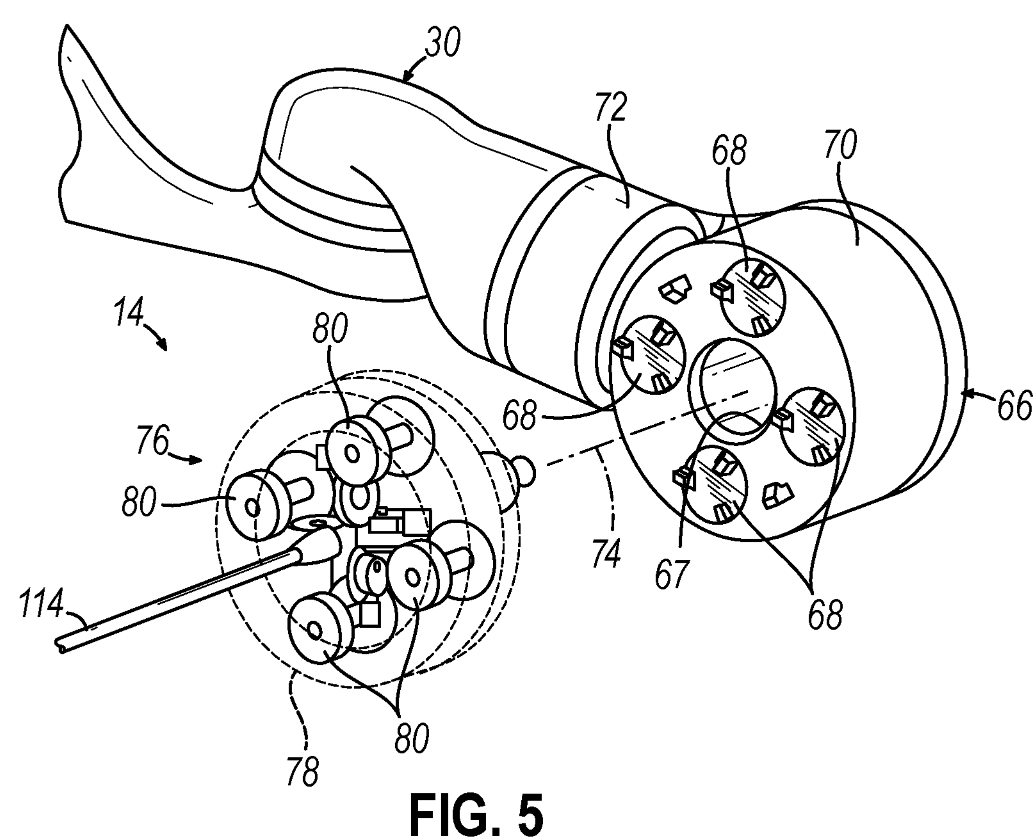
FIG. 5 depicts a partially exploded perspective view of the robotic arm of FIG. 4 having an instrument driver and a first illustrative surgical instrument.

FIG. 5 shows one example of instrument driver (66) in greater detail with RF energy surgical instrument (14) removed therefrom. Given the present instrument-based insertion architecture shown with reference to surgical instrument (14), instrument driver (66) further includes a clearance bore (67) extending entirely therethrough so as to movably receive a portion of surgical instrument (14) as discussed below in greater detail. Instrument driver (66) may also be referred to herein as an "instrument drive mechanism," an "instrument device manipulator," or an "advanced device manipulator" (ADM). Instruments may be designed to be detached, removed, and interchanged from instrument driver (66) for individual sterilization or disposal by the medical professional or associated staff. In some scenarios, instrument drivers (66) may be draped for protection and thus may not need to be changed or sterilized.

Each instrument driver (66) operates independently of other instrument drivers (66) and includes a plurality of rotary drive outputs (68), such as four drive outputs (68), also independently driven relative to each other for directing operation of surgical instrument (14). Instrument driver (66) and surgical instrument (14) of the present example are aligned such that the axes of each drive output (68) are parallel to the longitudinal axis of surgical instrument (14). In use, control circuitry (not shown) receives a control signal, transmits motor signals to desired motors (not shown), compares resulting motor speed as measured by respective encoders (not shown) with desired speeds, and modulates motor signals to generate desired torque at one or more drive outputs (68).

In the present example, instrument driver (66) is circular with respective drive outputs (68) housed in a rotational assembly (70). In response to torque, rotational assembly (70) rotates along a circular bearing (not shown) that connects rotational assembly (70) to a non-rotational portion (72) of instrument driver (66). Power and controls signals may be communicated from non-rotational portion (72) of instrument driver (66) to rotational assembly (70) through electrical contacts therebetween, such as a brushed slip ring connection (not shown). In one example, rotational assembly (70) may be responsive to a separate drive output (not shown) integrated into non-rotatable portion (72), and thus not in parallel to the other drive outputs (68). In any case, rotational assembly (70) allows instrument driver (66) to rotate rotational assembly (70) and drive outputs (68) in conjunction with surgical instrument (14) as a single unit around an instrument driver axis (74).

Any systems described herein, including table-based robotic system (28), may further include an input controller (not shown) for manipulating one or more instruments. In some embodiments, the input controller (not shown) may be coupled (e.g., communicatively, electronically, electrically, wirelessly and/or mechanically) with an instrument such that manipulation of the input controller (not shown) causes a corresponding manipulation of the instrument e.g., via master slave control. In one example, one or more load cells (not shown) may be positioned in the input controller such that portions of the input controller (not shown) are capable of operating under admittance control, thereby advantageously reducing the perceived inertia of the controller while in use.

In addition, any systems described herein, including table-based robotic system (28) may provide for non-radiation-based navigational and localization means to reduce exposure to radiation and reduce the amount of equipment within the operating room. As used herein, the term "localization" may refer to determining and/or monitoring the position of objects in a reference coordinate system. Technologies such as pre-operative mapping, computer vision, real-time electromagnetic sensor (EM) tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

C. First Illustrative RF Energy Surgical Instrument

Figure 6A:
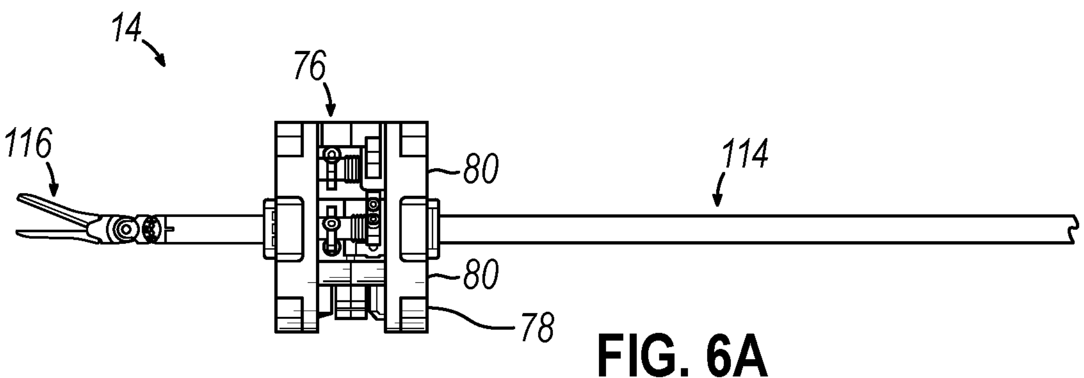
FIG. 6A depicts a side elevational view of the surgical instrument of FIG. 5 in a retracted position.
Figure 6B:
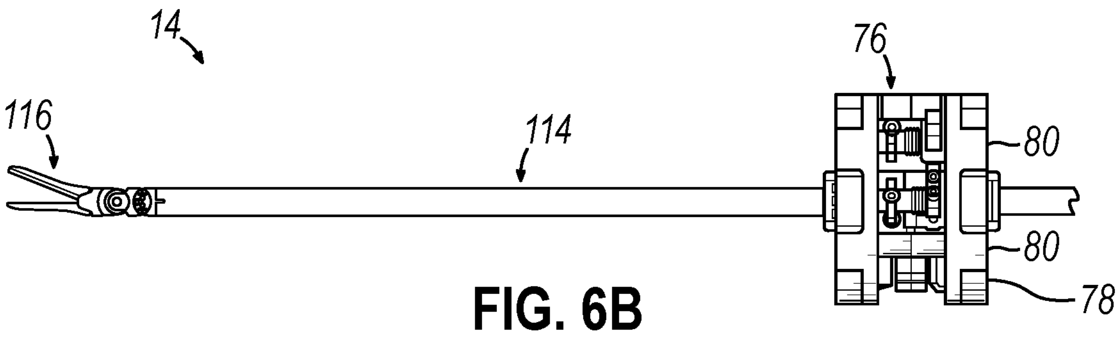
FIG. 6B depicts the side elevational view the surgical instrument similar to FIG. 6A, but in an extended position.

With respect to FIGS. 5-6B and in cooperation with instrument driver (66) discussed above, surgical instrument (14) includes an elongated shaft assembly (114) and an instrument base (76) with an attachment interface (78) having a plurality of drive inputs (80) configured to respectively couple with corresponding drive outputs (68). Shaft assembly (114) of RF energy surgical instrument (14) extends from a center of base (76) with an axis substantially parallel to the axes of the drive inputs (80) as discussed briefly above. With shaft assembly (114) positioned at the center of base (76), shaft assembly (114) is coaxial with instrument driver axis (74) when attached and movably received in clearance bore (67). Thus, rotation of rotational assembly (70) causes shaft assembly (114) of RF energy surgical instrument (14) to rotate about its own longitudinal axis while clearance bore (67) provides space for translation of shaft assembly (114) during use.

To this end, FIGS. 6A-6B show surgical instrument (14) having the instrument-based insertion architecture as discussed briefly above. Surgical instrument (14) includes elongated shaft assembly (114), an end effector (116) connected to and extending distally from shaft assembly (114), and instrument base (76) coupled to shaft assembly (114). Notably, insertion of shaft assembly (114) is grounded at instrument base (76) such that end effector (116) is configured to selectively move longitudinally from a retracted position to an extended position, vice versa, and any desired longitudinal position therebetween. As used herein, the retracted position is shown in FIG. 6A and places end effector (116) relatively close and proximally toward instrument base (76), whereas the extended position is shown in FIG. 6B and places end effector (116) relatively far and distally away from instrument base (76). Insertion into and withdrawal of end effector (116) relative to the patient may thus be facilitated by RF energy surgical instrument (14), although it will be appreciated that such insertion into and withdrawal may also occur via robotic arms (see FIG. 5) in one or more examples.

While various features configured to facilitate movement between end effector (116) and drive inputs (80) are described herein, such features may additionally or alternatively include pulleys, cables, carriers, such as a kinetic articulating rotating tool (KART), and/or other structures configured to communicate movement along shaft assembly (114). Moreover, while instrument base (76) is configured to operatively connect to instrument driver (66) for driving various features of shaft assembly (114) and/or end effector (116) as discussed below in greater detail, it will be appreciated that alternative examples may operatively connect shaft assembly (114) and/or end effector (116) to an alternative handle assembly (not shown). Such handle assembly (not shown) may include a pistol grip (not shown) in one example, configured to be directly gripped and manipulated by the medical professional for driving various features of shaft assembly (114) and/or end effector (116). The invention is thus not intended to be unnecessarily limited to use with instrument driver (66).

Turning to FIGS. 7A-8B, end effector (116) includes a first jaw (120) having a first electrode surface (121), a second jaw (122) having a second electrode surface (123), and a knife member (125) slidably disposed within a knife channel (124) cooperatively defined by first jaw (120) and second jaw (122). As will be described in greater detail below, end effector (116) of the current example in configured to grasp tissue with jaws (120, 122), seal tissue by applying bipolar RF energy to tissue via electrodes (121, 123), and sever tissue utilized knife member (125). In the current example, end effector (116) is suitably coupled to drive inputs (80) via cables and pulleys in order to suitably actuate components of end effector (116) in accordance with the description herein.

Figures 7A, 7B:
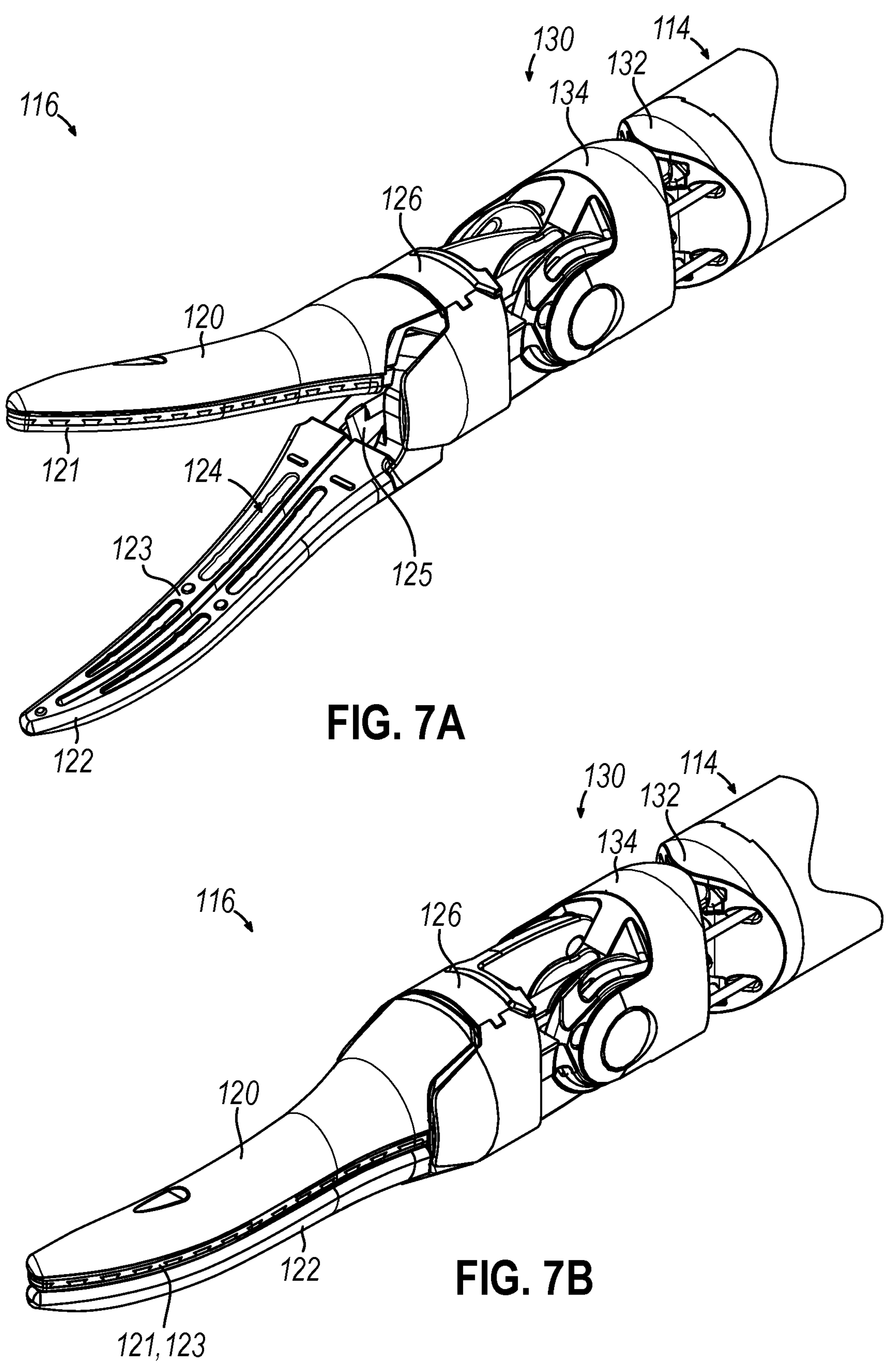
FIG. 7A depicts a perspective view of an end effector of the surgical instrument of FIG. 5, with jaws of the end effector in an open position.
FIG. 7B depicts a perspective view of the end effector of FIG. 7A, with the jaws of FIG. 7A in a closed position.

As shown between FIGS. 7A-7B, first jaw (120) and second jaw (122) are pivotally coupled to each other such that jaws (120, 122) may actuate between an open position and a closed position in order to grasp tissue. In the current example, jaws (120, 122) are operatively attached to a clevis assembly (126) configured to translate to thereby pivot jaws (120, 122) between the open position and the closed position. While a clevis assembly (126) is utilized in the current example, any other suitable structures may be utilized in order to drive jaws (120, 122) between the open and closed positions as would be apparent to one skilled in the art in view of the teachings herein.

Figure 7C:
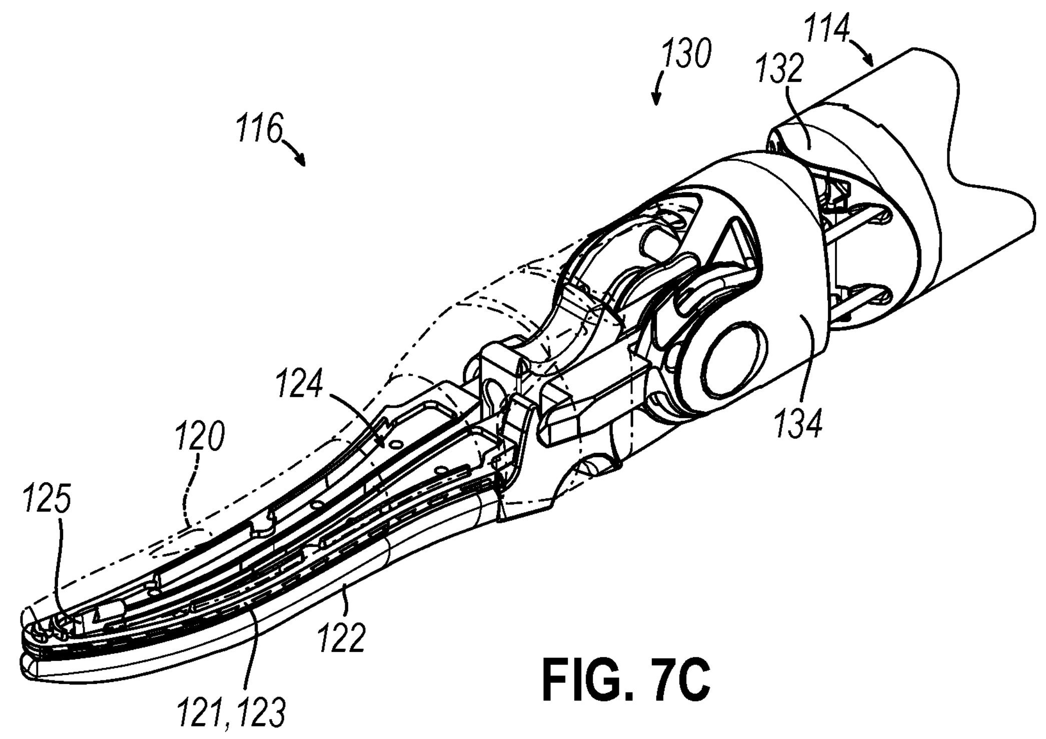
FIG. 7C depicts a perspective view of the end effector of FIG. 7A, with the jaws of FIG. 7A in a closed position and a knife member in the extended position, with one jaw shown in phantom.

As best shown between FIGS. 7B-7C, while jaws (120, 122) are in the closed position, knife member (125) may be driven distally along the path defined by knife channel (124) from a proximal position (as illustrated in FIG. 7A) and a distal position in order to sever tissue grasped by jaws (120, 122). Once knife member (125) reaches the distal position within knife channel (124) in order to suitably sever tissue, knife member (125) may then be retracted within knife channel (124) back into the proximal position. In instances where a cable is used to actuate knife member (125) within knife channel (124) between the proximal and distal positions, such a cable may be attached to a first drive input (80) dedicated to distally actuating knife member (125); while the cable may also be attached to a second drive input (80) dedicated to proximally actuating knife member (125).

Electrode surfaces (121, 123) may be activated during any suitable time at which jaws (120, 122) interact with tissue in order to apply bipolar RF energy to tissue. For example, electrode surfaces (121, 123) may be activated after knife member (125) severs tissue in order to seal the recently severed tissue grasped between jaws (120, 122). As another illustrative example, electrode surfaces (121, 123) may be activated prior to knife member (125) severing tissue. As yet another illustrative example, electrode surface (121, 123) may be activated in order to cauterize tissue without cutting tissue.

In the current example, electrode surface (121) is an electrode body attached on the underside of jaw (120); while jaw (122) is formed from a suitable material in order to act as electrode surface (123). For example, jaw (122) may be formed of a metal material and be in connection with a ground wire; while electrode body forming electrode surface (121) is attached the underside of jaw (120) and in communication with a hot wire. Once suitably activated, RF energy may be transmitted between electrode surfaces (121, 123) in order to further transmit such RF energy through tissue.

Electrode surfaces (121, 123) may have any suitable configuration as would be apparent to one skilled in the art in view of the teachings herein. While in the current example, electrode surfaces (121, 123) are configured to deliver bipolar RF energy to tissue, it should be understood that end effector (116) may be configured to deliver any other suitable type of therapeutic energy to tissue as would be apparent to one skilled in the art in view of the teachings herein.

Figure 8A:
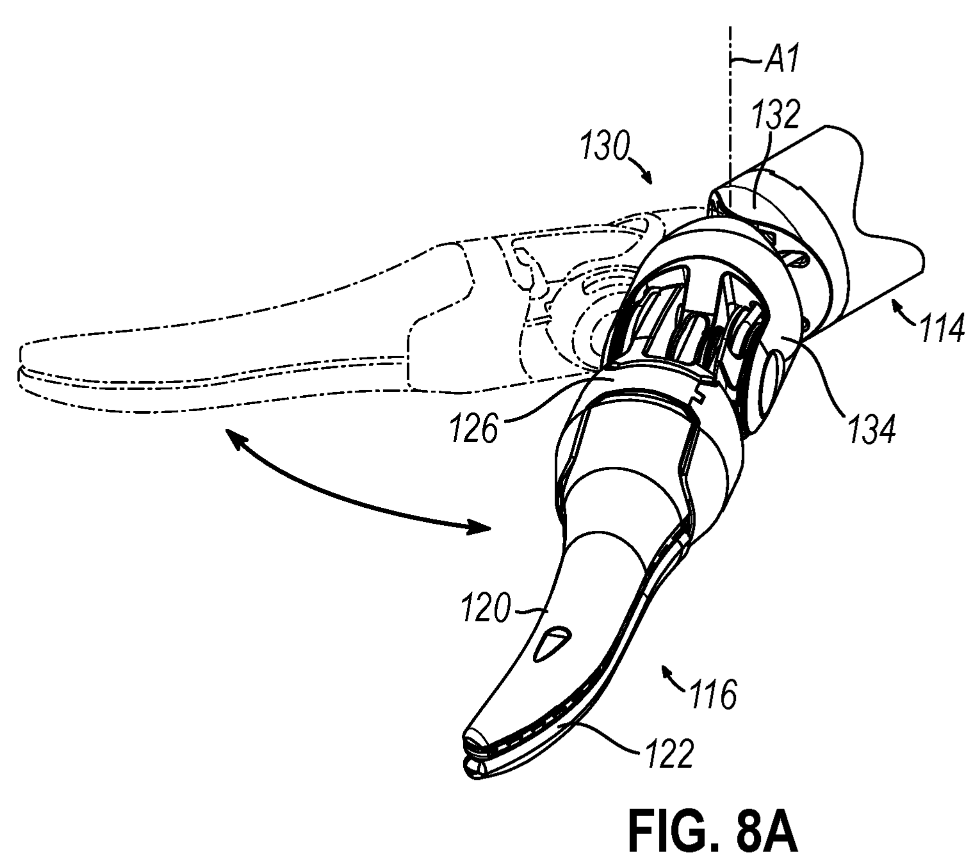
FIG. 8A depicts a perspective view of the end effector of FIG. 7A in a first articulated position.
Figure 8B:
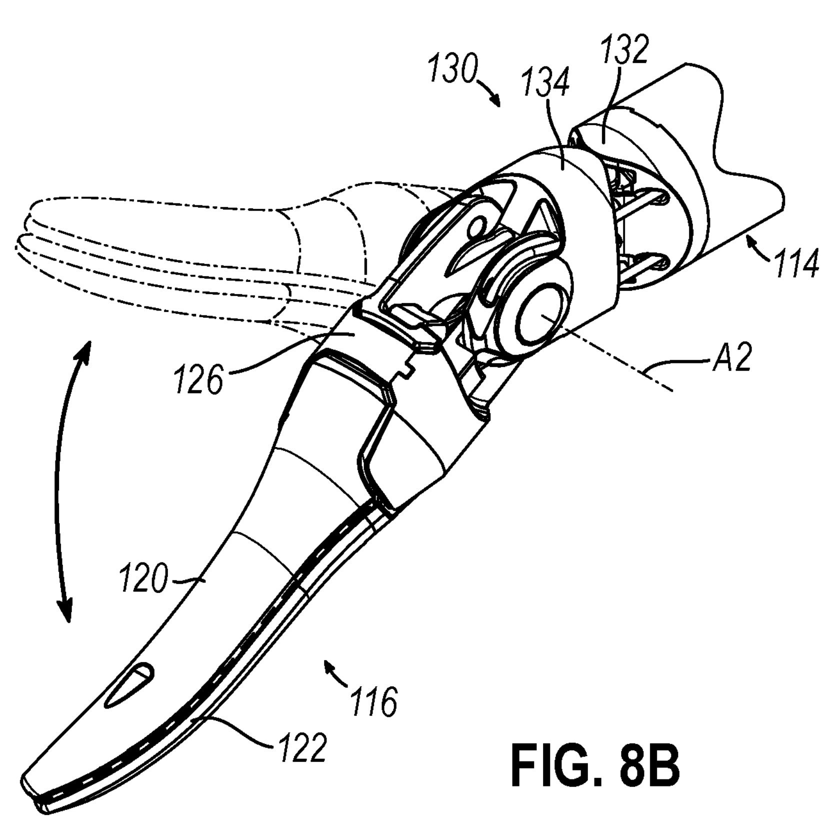
FIG. 8B depicts a perspective view of the end effector of FIG. 7A in a second articulated position.

Turning to FIGS. 8A-8B, end effector (116) also includes an articulation assembly (130) configured to deflect jaws (120, 122) relative to the longitudinal axis of shaft assembly (114). In the current example, articulation assembly (130) include a proximal camming body (132) associated with a distal end of shaft assembly (114) and a distal camming body (134) associated with a proximal end of end effector (116). Camming bodies (132, 134) are configured to engage each other as jaws (120, 122) are articulated about a first axis (A1), as shown in FIG. 8A. In some instances, articulation assembly (130) may be configured to pivot both jaws (120, 122) about a second axis (A2), as shown in FIG. 8B.

II. Illustrative Surgical Instrument with Bailout and Lockout Features

In some instances, it may be desirable to decouple surgical instrument (14) from a respective robotic arm (20, 32) during illustrative use of surgical instrument (14) in accordance with the description herein. For example, it may be desirable to decouple instrument base (76) of surgical instrument (14) from instrument driver (66) of robotic arm (32) during a surgical procedure such that drive inputs (80) of instrument (14) are operatively detached from respective rotary drive outputs (68) of instrument driver (66). In such instances, manually controllable features on surgical instruments (14) may be utilized to control and manipulate end effector (16) in preparation for suitable removal from the surgical site. Such a decoupling of surgical instruments (14) during illustrative use may be referred to as "bailing out" or a "bailout." For illustrative purposes, during illustrative use of instrument (14), jaws (120, 122) of end effector (16) may become stuck in the closed position while grasping tissue such that rotary drive outputs (68) are undesirably inhibited from actuating jaws (120, 122) back into the open position. Therefore, it may be desirable to decouple rotary drive output (68) from instrument (14), utilize a manually controlled feature on instrument to release jaws (120, 122) from tissue, and then suitably remove instrument (14) from the surgical site.

Providing a feature that allows for a suitable bailout between instrument (14) and instrument driver (66) may be difficult. The force required to activate a bailout feature should be sufficiently low enough such that an operator may manually decouple instrument (14) from instrument driver (66). However, if the force required to activate a bailout feature is too low, accidental contact or other forces may inadvertently activate the bailout features unintentionally. In other words, it may be desirable to have a bailout feature that is easily controllable to allow an operator to manually decouple drive inputs (80) from rotary drive outputs (68), yet inhibit unintentional activation of such a bailout feature. Therefore, it may be desirable to have a bailout feature that requires a first, intentional, step that initially renders the bailout feature operable; and a subsequent activation step that drives the instrument (14) out of engagement with instrument drier (66) (e.g., bails instruments (14) out).

Figure 9A:
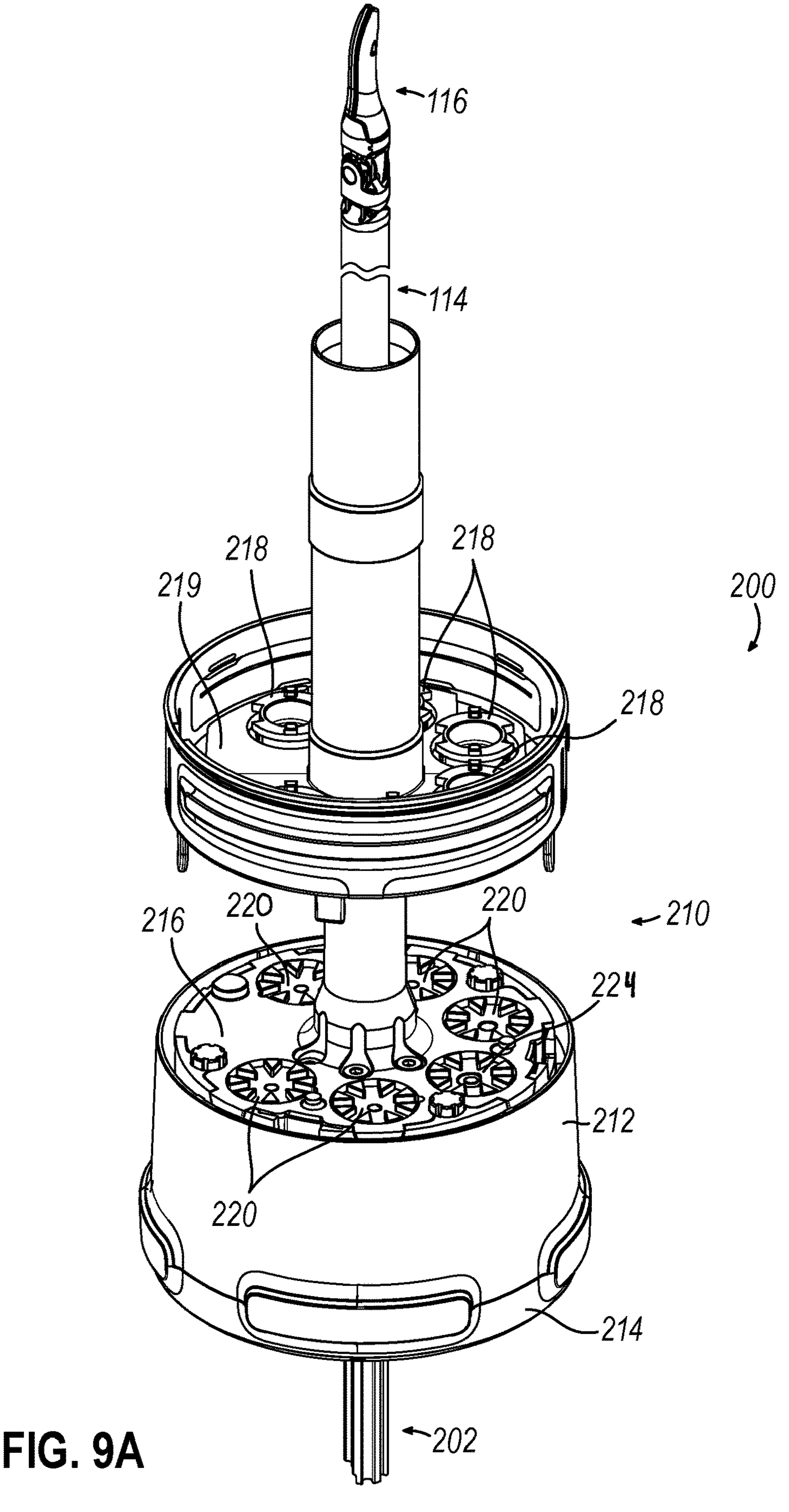
FIG. 9A depicts a bottom perspective view of a second illustrative surgical instrument decoupled from a sterile adapter accessory.
Figure 9B:
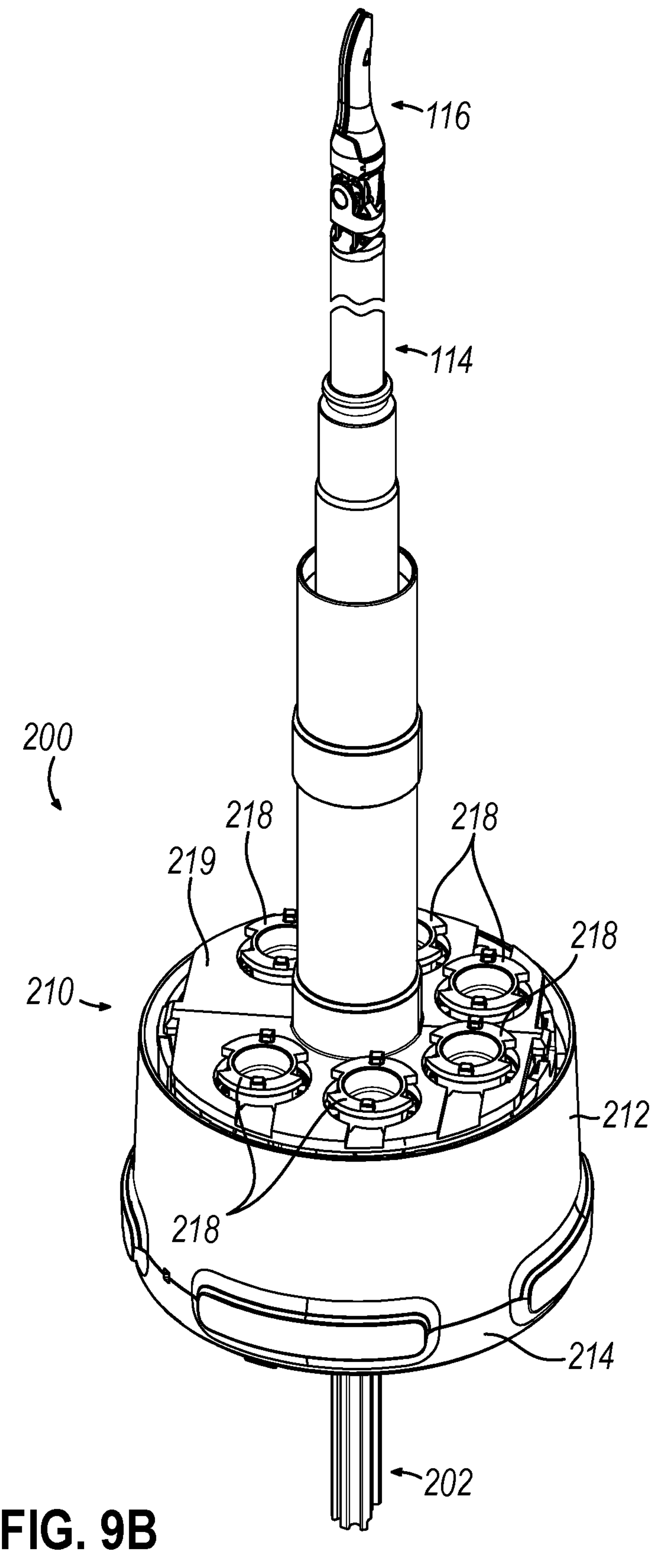
FIG. 9B depicts a bottom perspective view of the surgical instrument of FIG. 9A coupled with the sterile adapter accessory of FIG. 9A.
Figure 10:
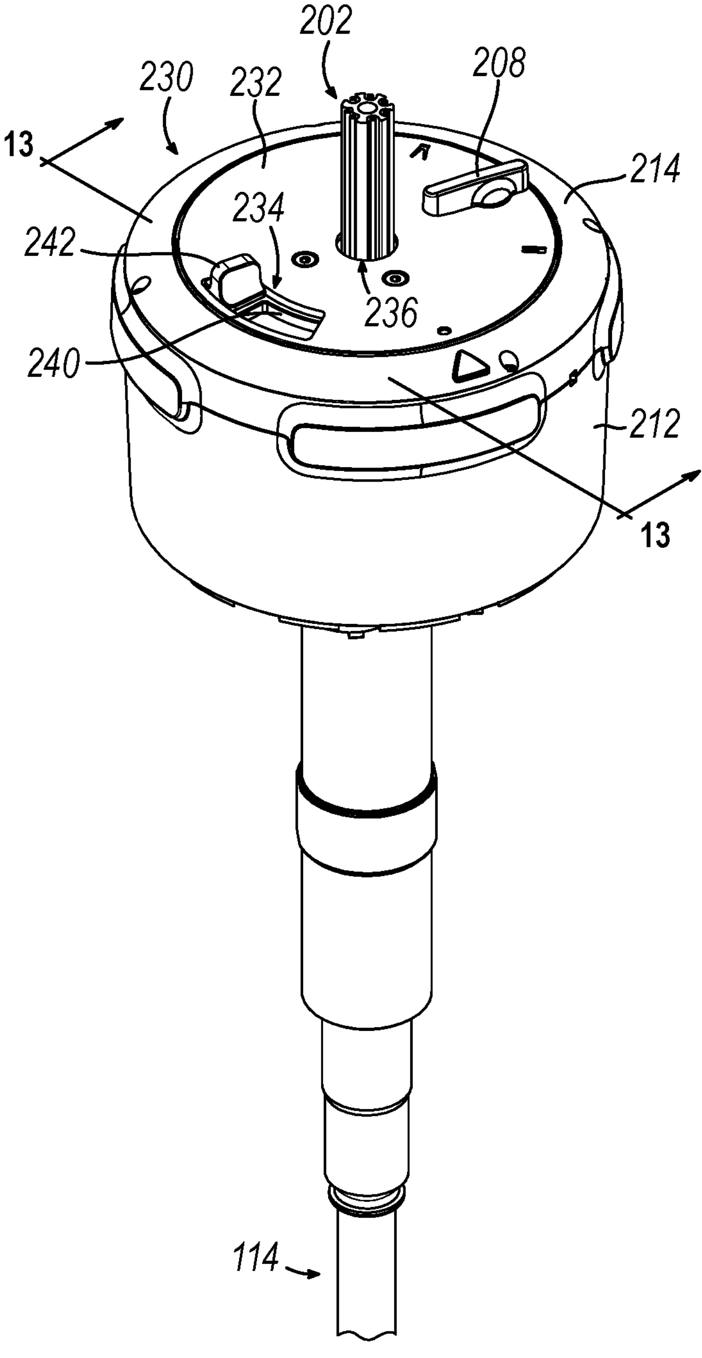
FIG. 10 depicts a top perspective view of the surgical instrument of FIG. 9A.

FIGS. 9A-10 show an alternative RF energy surgical instrument (200) that may be used in replacement of RF energy surgical instrument (14) described above, in accordance with the description herein. RF energy surgical instrument (200) is substantially similar to instrument (14) described above, with differences elaborated below. As will be described in greater detail below, instrument (200) includes a two-step bailout assembly (230) configured to drive instrument (200) out of operable engagement with instrument drive (66) to thereby bailout instrument (200).

Instrument (200) includes an instrument base (210), shaft assembly (114), and end effector (116). As shown between FIGS. 9A-9B, instrument (200) is configured to attach to a sterile adapter (219), which acts as an intermediary between a suitable instrument driver (66) of a robotic arm (32) and instrument (200). End effector 1160) and shaft assembly (114) may be inserted through a sheath of sterile adapter (219) until sterile adapter (219) suitably attaches to instrument base (210). Sterile adapter (219) includes a plurality of motor engagement caps (218) which are rotatably disposed within base of sterile adapter (219). Instrument base (210) is substantially similar to instrument base (76) described above, with differences elaborated below. In the current example, shaft assembly (114) includes a proximal shaft portion (202) extending proximally from instrument base (210). It should be understood that proximal shaft portion (202) actuates relative to instrument base (210) with the rest of shaft assembly (114) while being inserted and retracted in accordance with the description herein.

In the current illustrative example, instrument base (210) includes a plurality of drive input assemblies (220, 224) (see FIGS. 9A and 11) and an idler input assembly (222). Drive input assemblies (220, 224) are configured to operatively attach to a respective rotary drive output (68) of instrument driver (66). As will be describe in greater detail below, idler input assembly (222) is operatively attached to drive input assembly (224) via a coupling cable (225) (see FIG. 22) such that rotation of drive input assembly (224) drives corresponding rotation of idler input assembly (222). Input assemblies (222, 224) are configured to cooperatively actuate knife member (125) within jaws (120, 122) in accordance with the description herein.

Drive input assemblies (220, 224) may be substantially similar to drive inputs (80) described above, with differences elaborated herein. Drive input assemblies (220, 224) are configured to receive rotational motion of drive outputs (68) in order to suitably control end effector (116) in accordance with the description herein. It should be understood that six drive input assembly (220, 224) are shown in the current example such that instrument driver (66) may have six corresponding drive outputs (68) to suitably engage instrument (200).

Instrument base (210) also includes one or more manual rotational input features (208). Manual rotational input features (208) are operatively attached to one or more drive input assemblies (220, 224). An operator may rotate manual rotational input feature (208) in order to suitably control end effector (216) while drive input assemblies (220, 224) are detached from drive outputs (68). In other words, manual rotation input feature (208) allows an operator to control motion of end effector (216) while instrument (200) is bailed out from robotic arm (32).

As shown in FIG. 9, a motor engagement cap (218) is attached to a respective drive input assembly (220, 224). Motor engagement caps (218) act as an intermediary between respective drive input assemblies (220, 224) and respective rotary drive outputs (68) of instrument driver (66). Therefore, motor engagement caps (218) may help maintain a sterile barrier between instrument base (210) and instrument drive (66) while also transmitting rotational motion from drive outputs (68) onto a respective drive input assembly (220, 224) of instrument (200) in order to operatively control end effector (116) in accordance with the description herein. As will be described in greater detail below, motor engagement caps (218) are operable to detach from input assemblies (220, 224) in response to instrument (200) bailing out. While motor engagement caps (218) are used in the current example, this is merely optional. In some instances, drive input assemblies (220, 224) are attached to respective rotary drive outputs (68) either directly or with some other sterilizing intermediary interposed therebetween.

Instrument base (210) also includes a distal housing (212), a proximal latch ring (212), a chassis assembly (216), and a two-stage bailout assembly (230). Distal housing (212) and proximal latch ring (212) contain chassis assembly (216). Chassis assembly (216) supports various components of instrument base (210) by acting as a mechanical ground. Chassis assembly (216) supports various moving components of instrument base (210), such as drive input assemblies (220, 224), idler input assembly (222), and other suitable moving components as would be apparent to one skilled in the art in view of the teachings herein.

Figure 11:
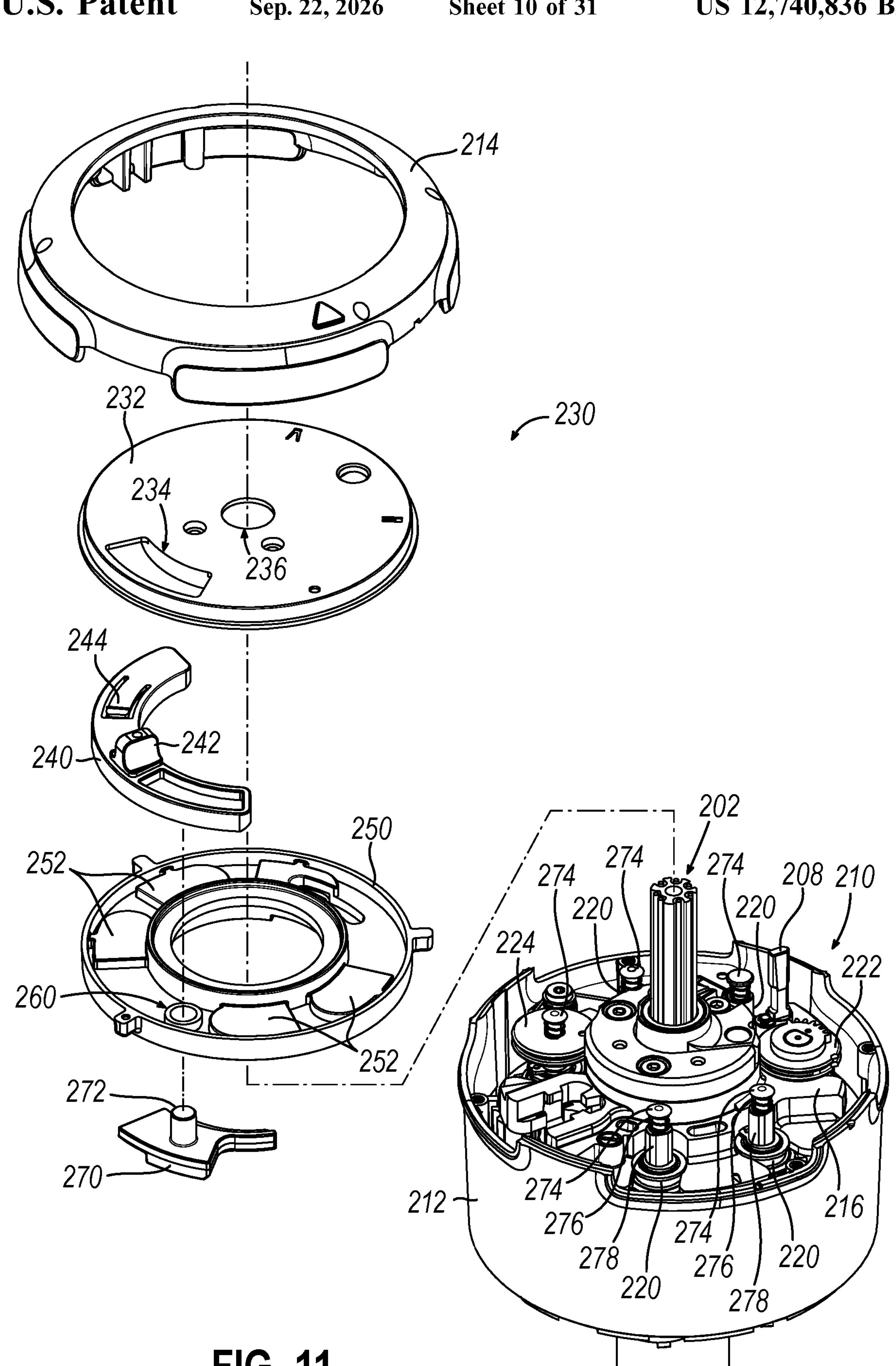
FIG. 11 depicts an exploded view of an instrument base of the surgical instrument of FIG. 9A, including a two-stage bailout assembly.

As mentioned above, two-stage bailout assembly (230) is configured to bailout instrument (200) from operable engagement with instrument driver (66). Turning to FIG. 11, two-stage bailout assembly (230) includes a cap (232), a sliding body (240), a rotating cam plate (250), a bailout coupling body (270), and a plurality of pogo pins (274) biased proximally by a respective spring (276) interposed between pin (274) and a respective collar (278). As will be described in greater detail below, sliding body (240) is configured to actuate from a pre-bailout position (see FIG.

Figure 13A:
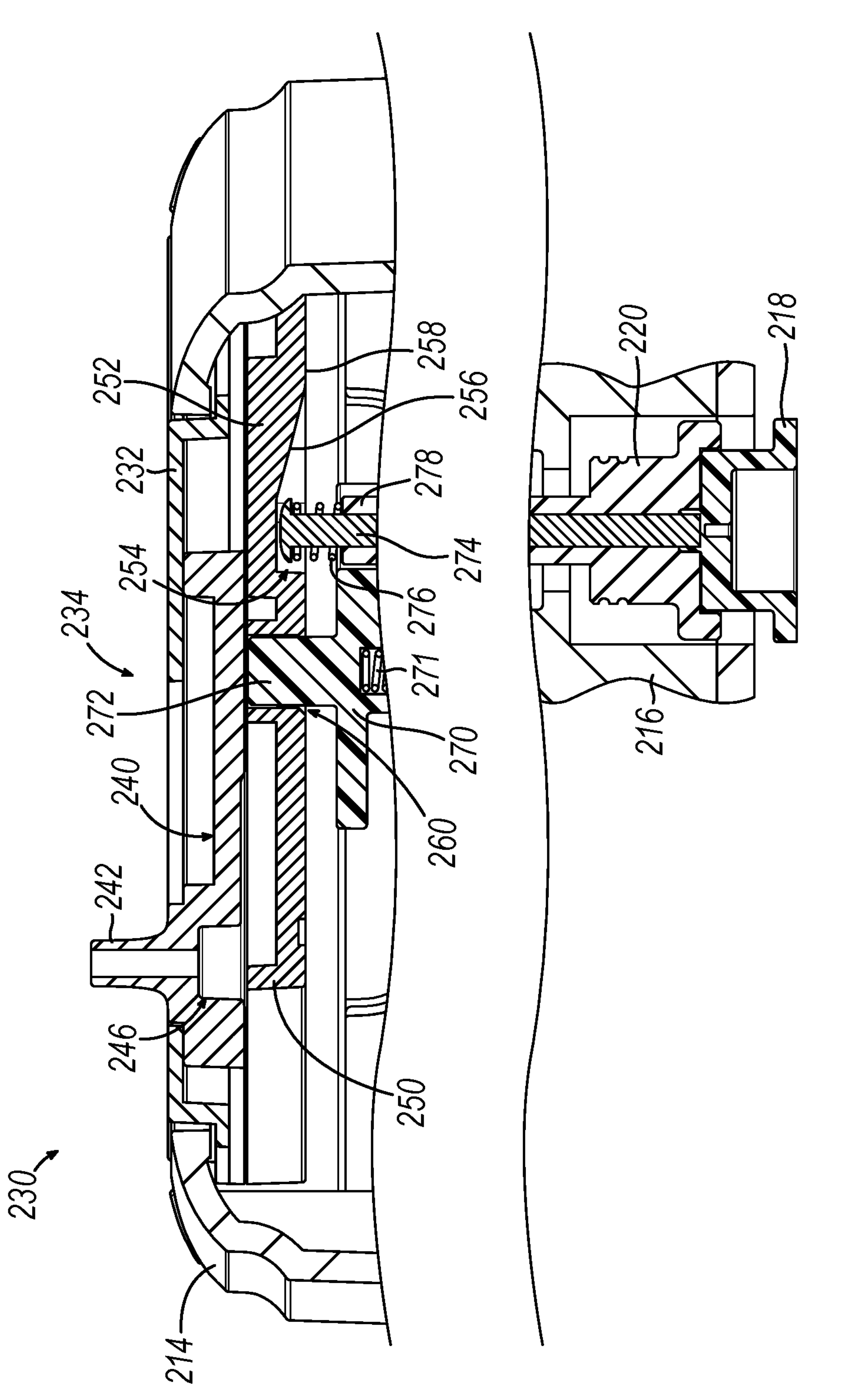
FIG. 13A depicts a cross-sectional view, taken along line 13-13 of FIG. 10, of the two-stage bailout assembly of FIG. 11 in a pre-bailout configuration.
Figure 13B:
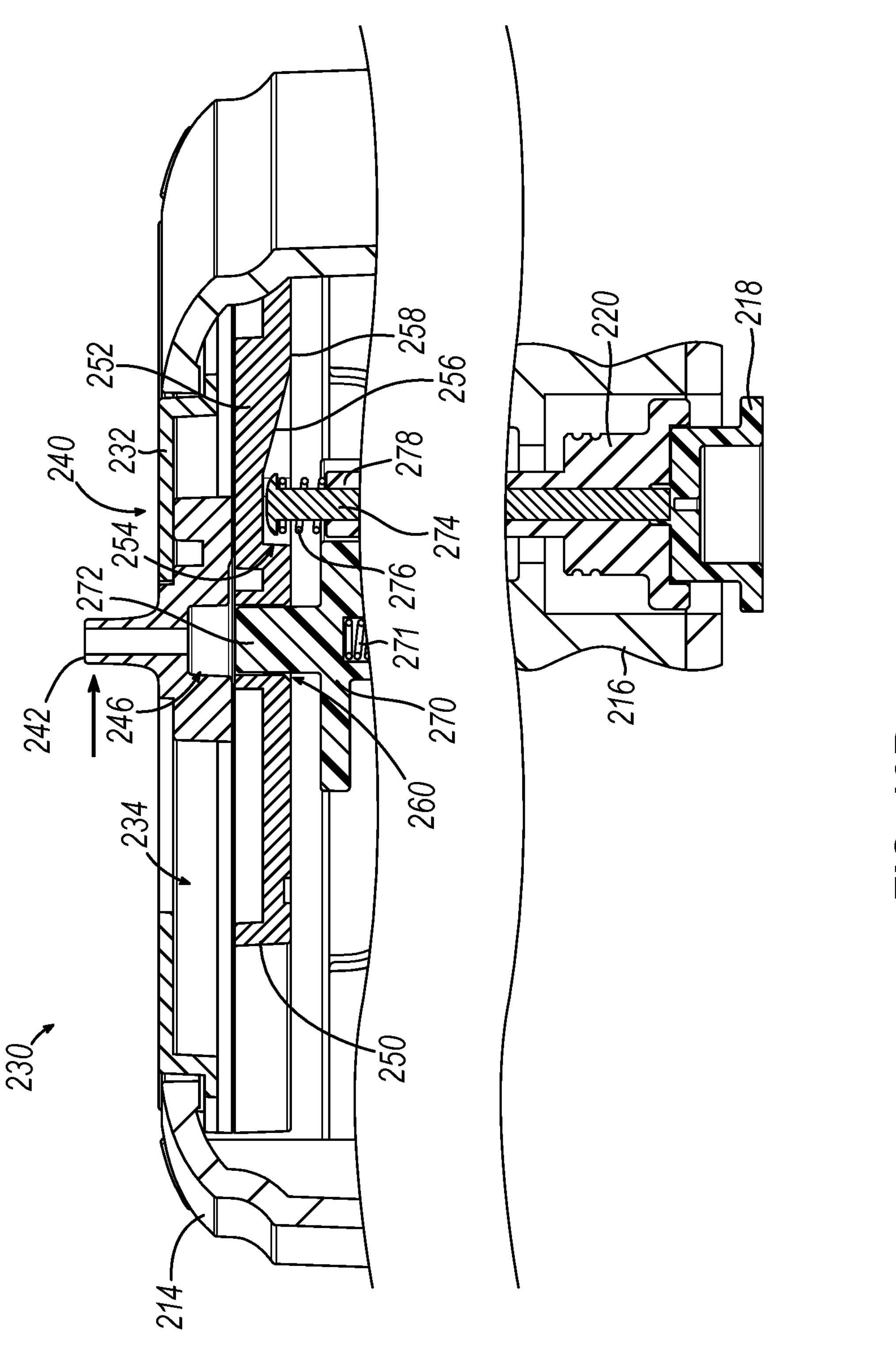
FIG. 13B depicts a cross-sectional view, taken along line 13-13 of FIG. 10, of the two-stage bailout assembly of FIG. 11 in an engaged configuration with a bailout coupling body in a pre-deployed position.
Figure 13C:
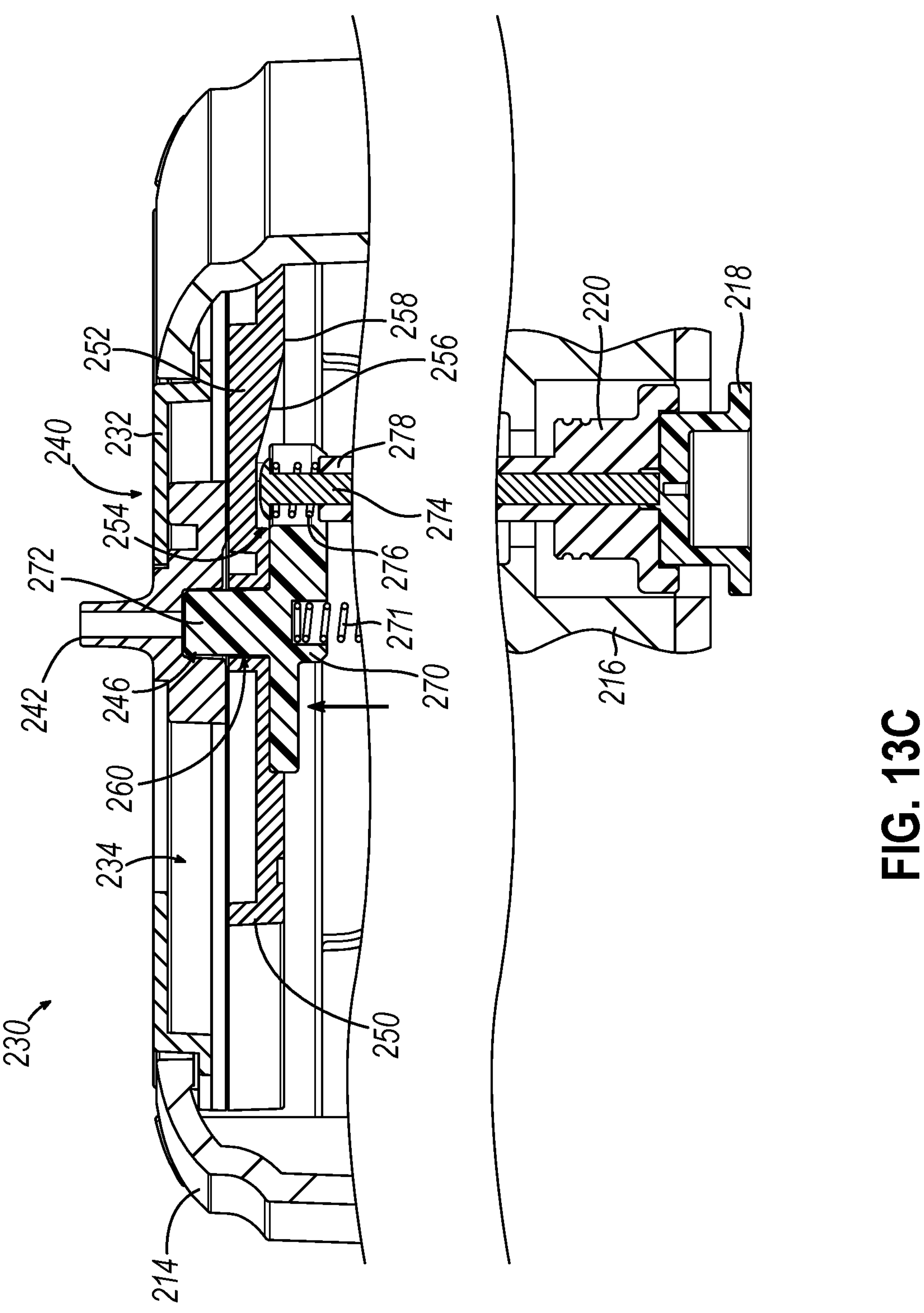
FIG. 13C depicts a cross-sectional view, taken along line 13-13 of FIG. 10, of the two-stage bailout assembly of FIG. 11 in an engaged configuration with a bailout coupling body in a deployed position.

13A) into an engaged position (see FIGS. 13B-13C). In the pre-bailout position, two-stage bailout assembly (230) is inhibited from inadvertently bailing out instrument (200). Once in the engaged position, sliding body (240) may further be actuated into a bailout configuration (see FIG. 13D), which in turn drives motor engagement caps (218) out of engagement with a respective drive input assembly (220, 224), thereby bailing instrument (200) out of engagement with instrument driver (66) of robotic arm (32). Therefore, in order to bail instrument out (200), an operator is forced to complete two actuation stages of sliding body (240).

As shown in FIG. 10, cap (232) is interposed between portions of housing (212) and latching ring (214) such that cap is (232) attached chassis assembly (216). Housing (212) and latch ring (214) may be configured to suitably rotate and translate relative to cap (232) and chassis assembly (216) during a bailout process in accordance with the description herein. Cap (232) defines a shaft through hole (236) dimensioned to slidably receive a proximal shaft portion (202). Cap (232) also defines an arched slot (234) that slidably contains a gripping tab (242) of sliding body (240).

Arched slot (234) defines a path of travel which sliding body (240) may actuate relative to cap (232). As will be described in greater detail below, sliding body (240) may actuate along arched slot (234) in a first direction from a pre-bailout position into an engaged position in order to suitably couple to cam plate (250), and then actuate in a second direction (e.g., back toward the original position of sliding body (240)) into a bailout configuration in order to rotate cam plate (250).

Sliding body (240) contains gripping tab (242) and a frictional braking force generator in the form of a leaf spring (244). Portions of sliding body (240) located under gripping tab (242) are interposed between cap (232) and cam plate (250). Gripping tab (242) extends upwardly through arched slot (234) a sufficient distance in order to allow an operator to easily grasp gripping tab (242) for use in accordance with the description herein. Leaf spring (244) engages cap (232) in order to provide a sufficient frictional braking force onto sliding body (240), thereby inhibiting sliding body (240) from inadvertently moving relative to cap (232). As shown in FIGS. 13A-13D, the underside of sliding body (240) defines a recessed area (246). Recessed area (246) is dimensioned to receive a pin (272) of bailout coupling body (270). In particular, recessed area (246) is positioned along sliding body (240) such that recessed area (246) is directly adjacent to pin (272) of bailout coupling body (270) when gripping tab (242) is actuated in the first direction along arched slot (232) a suitable distance into the engaged position. Prior to recessed area (246) being directly adjacent to pin (272) of bailout coupling body (270), an underside of sliding body (240) may urge pin (272) downward (see FIG. 13A), thereby overcoming a biasing force acting on bailout coupling body (272) provided via spring (271).

Cam plate (250) includes a plurality of camming sections (252) and a pin through hole (260). Cam plate (250) may be coupled to housing (212) such that housing (212) and latch ring (214) rotate with cam plate (250) in accordance with the description herein. Pin through hole (260) houses pin (272) of bailout coupling body (270). Pin (272) is slidably contained within pin through hole (260) such that pin (272) is configured to actuate vertically (with reference to FIGS. 13A-13D) relative to cam plate (250), but such that rotation (or other suitable lateral movement) of bailout coupling body (270) drives corresponding rotation of cam plate (250). As will be described in greater detail below, once pin (272) is directly adjacent to recessed area (246) of sliding body (240), pin (272) is driven upward within pin through hole (260) via spring (271) such that pin (272) is also housed within recessed area (246) of sliding body (240). When pin (272) is housed within recessed area (246), sliding body (240) is configured drive movement of both bailout coupling body (270) and cam plate (250).

Figure 12:
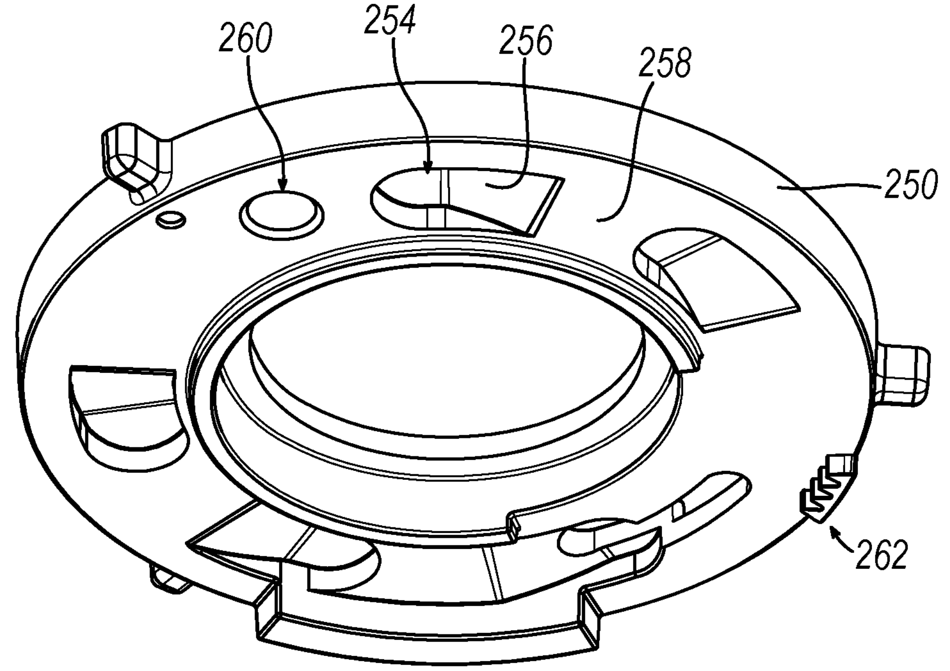
FIG. 12 depicts an exploded view of a cam plate of the two-stage bailout assembly of FIG. 11.

Turning to FIG. 12, each camming section (252) defines a recessed pogo pin housing (254) at least partially defined by a sloped camming surface (256). Sloped camming surfaces (256) also terminate into an interior surface (258) of cam plate (250). Pogo pin housings (254) are dimensioned to initially house a terminating end of pogo pin (274) (see FIGS. 13A-13C). In particular, pogo pin housing (254) is configured to house the terminating end of pogo pin (274) prior to use of two-step bailout assembly (230). As will be described in greater detail below, camming surface (256) is configured to engage and drive pogo pin (274) downward, overcoming the upward biasing force of spring (276) acting on pogo pin (274). As shown in FIGS. 13A-13D, each pogo pin (274) slidably extends through a respective drive input assembly (220, 224) or idler input assembly (222) such that a bottom end of each pogo pin (274) is directly adjacent to a respective motor engagement cap (218). As pogo pins (274) are driven downward via engagement with camming surface (256) (see FIGS. 13C-13D), pogo pins (274) urge motor engagement caps (218) away from a respective drive input assembly (220, 224) thereby decoupling and bailing out instrument (200) from rotary drive outputs (68).

As mentioned above, bailout coupling body (270) is biased upward via a biasing spring (271). While sliding body (240) is in the pre-bailout position (see FIG. 13A), biasing spring (271) urges pin (272) into engagement with the underside of sliding body (240). Once sliding body (240) is actuated into the engaged position (see FIG. 13B), pin (272) is driven into recessed area (246) such that sliding body (240) may acute both bailout coupling body (270) and cam plate (250).

Pogo pins (274) are slidably housed within a respective drive input assembly (220, 224). A bias spring (278) is interposed between a top end of pogo pin (274) and a collar (278) in order to bias pogo pins (274) upward. As shown in FIG. 13A, with pogo pins (274) in the upward position, a terminating bottom end of pogo pin (274) is adjacent to motor engagement cap (218), but not in sufficient engagement with motor engagement cap (218) to interfere with the coupling between motor engagement cap (218) and a respective drive input assembly (220, 224). The top end of pogo pin (274) is housed within recessed pogo housing (254) in the pre-bailout configuration such that cam plate (250) does not engage pogo pin (274) with a downwardly presented force. As mentioned above, in the bailout configuration, pogo pins (274) may be driven downward in response to rotation of cam plate via engagement with camming surface (256) (see FIGS. 13C-13D) such that pogo pins (274) urge motor engagement caps (218) away from a respective drive input assembly (220, 224); thereby decoupling and bailing out instrument (200) from rotary drive outputs (68).

FIGS. 13A-13D show an illustrative use of two-stage bailout assembly (230) in order to drive motor engagement caps (218) away from a respective drive input assembly (220, 224); thereby decoupling and bailing out instrument (200) from rotary drive outputs (68). As shown in FIG. 13A, sliding body (240) is in a pre-bailout configuration. In the pre-bailout configuration, gripping tab (242) is housed within arched slot (234) in the position shown in FIG. 10. Therefore, as shown in FIG. 13A, and underside of sliding body (240) urges pin (272) downward, overcoming the biasing force of spring (271). While in the position shown in FIG. 13A, bailout coupling body (272) may be partially engaged with a portion of chassis (216), thereby inhibiting rotation of cam plate (250) relative to pogo pins (274) in at least one rotational direction. If, during illustrative use, an operator desires to initiate a bailout sequence in order to decouple instrument (200) from rotary drive outputs (68), the operator may grasp tab (242) and actuate tab (242) within arched slot (234) toward the opposite end of arched slot (234).

As shown in FIG. 13B, once tab (242) is actuated within arched slot (234) into the engaged position, recessed area (246) may be suitably aligned with pin (272). As shown between FIGS. 13B-13C, with pin (272) suitably aligned with recessed area (246), the underside of sliding body (240) no longer overcomes the biasing force of spring (271). Therefore, spring (271) may urge pin (272) into recessed area (246) as shown in FIG. 13C. While in the position shown in FIG. 13C, bailout coupling body (270) may clear the position of chassis (216) inhibiting rotational movement of cam plate (250) relative to pogo pins (274) in the at least one rotation direction such that bailout coupling body (270) and cam plate (250) may now rotate relative to pogo pins (274). It should be understood that with pin (272) being housed within recessed area (246), sliding body (240) may drive movement of both bailout coupling body (270) and cam plate (250). At the moment shown in FIG. 13C, the operator has completed the first stage of a two-stage bailout process.

Next, the operator may grasp tab (242) and actuate tab (242) within arched slot (234) back toward the position shown in FIG. 10, thereby completing the second stage of the two-step bailout process. In instances where cam plate (250) is rotationally attached to housing (212) and latch ring (214), rather than grasping tab (242) directly, an operator may gasp housing (212) and/or latch ring (214) and rotate the outer cover of instrument base (210) to thereby drive movement of tab (242) within arched slot (232) back toward the position shown in FIG. 10. Actuation of tab (242) drives rotation of cam plate (250) such that cam surface (256) abuts against pogo pin (274). Cam surface (256) engages the top end of pogo pin (274), thereby overcoming the biasing force of spring (276) and driving pogo pin (274) downward. Downward actuation of pogo pin (274) forces the bottom end of pogo pin (274) into engagement with motor engagement cap (218), thereby driving motor engagement caps (218) out of suitable engagement with drive input assembly (220, 224) such that instrument (200) is effectively bailed out and not in operative engagement with rotary drive outputs (68). Interior surface (258) may remain engaged with the top end of pogo pins (274), thereby maintaining the position of pogo pins (274) as shown in FIG. 13D.

Figure 13D:
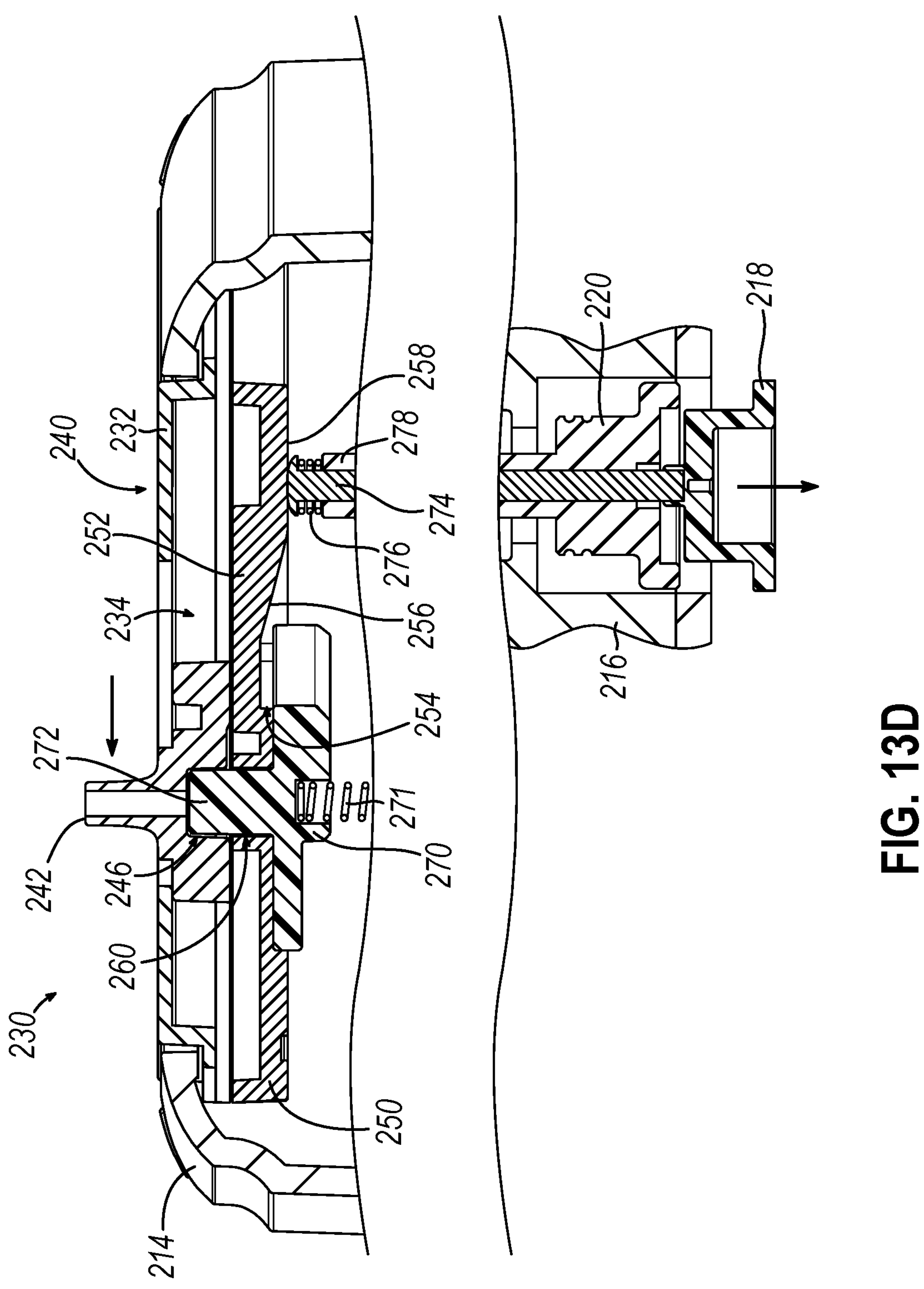
FIG. 13D depicts a cross-sectional view, taken along line 13-13 of FIG. 10, of the two-stage bailout assembly of FIG. 11 in a bailout configuration.

With instrument (200) effectively decoupled from motor engagement caps (218) and rotary drive outputs (68), as shown in FIG. 13D, an operator may utilize manual rotation input feature (208) in order to actuate end effector (116) into a desired position for retraction of end effector (116) from the surgical site.

It should be understood that in order for an operator to initiate the bailout functionality of two-stage bailout assembly (230), the operator first actuates sliding body (240) in a first direction from the pre-bailout position into the engagement position, thereby signaling the operator's intention of performing a bailout. In order to actuate sliding body into the engagement position, the operator must actuate sliding body (240) with sufficient force to overcome the fictional braking force providing by leaf spring (244). Then, the operator must actuate sliding body (240) back toward the initial position into the bailout position in order to complete the bailout process. This two-stage process may allow the force required to drive bailout assembly (230) to be reduced, thereby ensuring an operator may easily generate the necessary force for a successful bailout. Additionally, the two-stage process may allow the force required to drive bailout assembly (230) to be reduced while also inhibiting the chances of inadvertently initiating a bailout process.

III. Illustrative Shaft Insertion Lockout Assembly

As mentioned above, shaft assembly (114) and end effector (116) may be proximally retracted and distally advanced relative to instrument base (210). A drive input assembly (220) (see FIG. 11) may be operatively engaged with shaft assembly (114) such that rotation of drive input assembly (220) in a first rotational direction may distally advance shaft assembly (114) and end effector (116) relative to instrument base (210); while rotation of drive input assembly (220) in a second, opposite, rotational direction may proximally retract shaft assembly (114) and end effector (116) relative to instrument base (210). Prior to initiating a bailout process, as illustrated above, it may be desirable to be able to both distally advance and proximally retract shaft assembly (114) and end effector (116) relative to instrument base (210) in order to better control the positioning of end effector (116) at a surgical site. However, after initiating a bailout process, it may be desirable to inhibit further distal insertion of shaft assembly (114) and end effector (116) relative to instrument base (210); while still allowing for proximal retraction of shaft assembly (114) in order to suitably remove end effector (116) from the surgical site. For example, after a successful bailout is performed, an operator may accidently engage a proximal portion (202) of shaft assembly (114) and inadvertently advance shaft assembly (114) in the surgical site. Additionally, it may be desirable to inhibit distal insertion of shaft assembly (114) and end effector (116) in all other instances where instrument (200) is not operatively coupled with a suitable robotic arm (32). For example, it may be desirable to inhibit accidental insertion of shaft assembly (114) and end effector (116) prior to coupling instrument (200) with robotic arm (32).

Figures 14A, 14B:
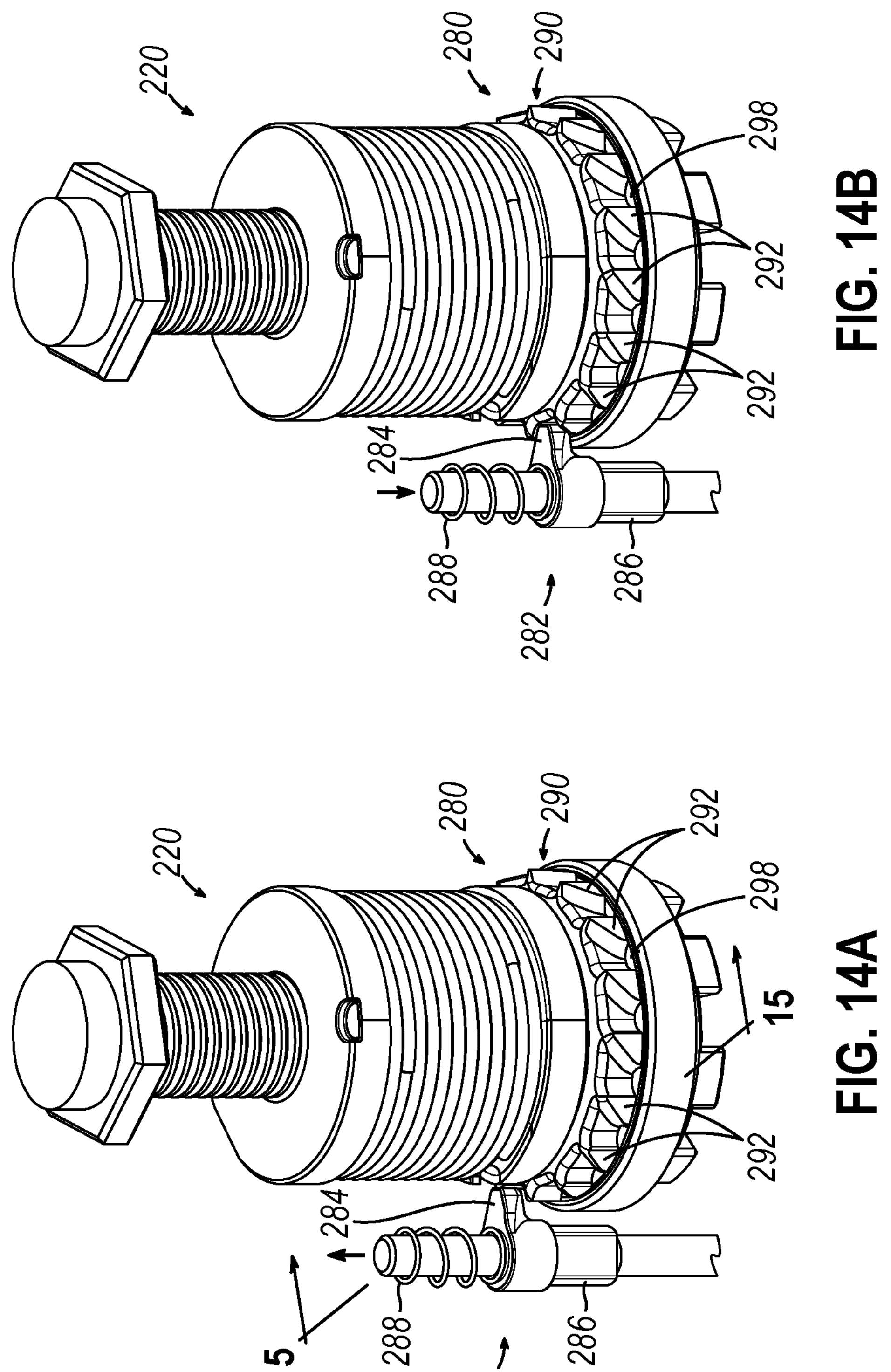
FIG. 14A depicts a perspective view of a shaft insertion lockout assembly in an unlocked configuration.
FIG. 14B depicts a perspective view of the shaft insertion lockout assembly of FIG. 14A in a locked configuration.

FIGS. 14A-14B show an illustrative shaft insertion lockout assembly (280) and a drive input assembly (220). Drive input assembly (220) is capable of rotating in a first rotational direction to distally advance shaft assembly (114) and end effector (116) relative to instrument base (210), and also rotating in a second, opposite, rotational direction to proximally retract shaft assembly (114) and end effector (116) relative to instrument base (210). As will be described in greater detail below, shaft insertion lockout assembly (280) is configured to allow drive input assembly (220) to rotate in both rotational directions prior to the bailout process; thereby allowing both proximal and distal movement of shaft assembly (114) relative to instrument base (210). As will also be described in greater detail below, shaft insertion lockout assembly (280) is configured to operatively engage drive input assembly (220) in response to a completed bailout such that drive input assembly (220) is inhibited from rotating in the direction associated with distal insertion of shaft assembly (114); yet enabling drive input assembly (220) to rotate in the direction associated with proximal retraction of shaft assembly (114).

Lockout assembly (280) includes a biased locking assembly (282) slidably coupled to chassis assembly (216), and a single direction lockout ring (290) fixed to the rotating component of drive input assembly (220). Biased locking assembly (282) is configured to actuate between an unlocked configuration (see FIG. 14A) and a locked configuration (see FIG. 14B).

Biased locking assembly (282) includes a single direction rotation lock (284) attached to a translating post (286). Translating post (286) is slidably coupled with chassis assembly (216) such that post (286) may vertically actuate relative to chassis assembly (216), but is otherwise substantially fixed relative to chassis assembly (216). A lockout spring (288) is interposed between translating post (286) and chassis assembly (216) such that lockout spring (288) biases single direction rotation lock (284) into the position shown in FIG. 14B.

In the unlocked configuration shown in FIG. 14A, single direction rotation lock (284) is operatively disengaged with single direction lockout ring (290), thereby allowing rotation of drive input assembly (220) in both rotational directions to advance and retract shaft assembly (114) in accordance with the description herein. In the position shown in FIG. 14A, a component associated with sterile adapter (219), motor engagement caps (218) or instrument drivers (66) may engage the underside of translating post (286) to thereby overcome the downward biasing force acting on post (286) via spring (288). Therefore, when instrument (200) is suitably attached to instrument driver (66), shaft assembly (114) may be inserted and retracted in accordance with the description herein. Once the bailout process is completed, as illustrated in the example above, or instrument (200) is decoupled from instrument driver (60), the component urging translating post (286) upward may be driven out of engagement with post (286) (e.g., by pogo pins (274) driving such a component) such that spring (288) may thereby bias single direction rotation lock (284) into operative engagement with single direction lockout ring (290), as shown between FIGS. 14A-14B and FIGS. 15A-15B. In other instances, a static component disengages post (286) in response to instrument (200) being decoupled with instrument driver (66). Such a static component may be associated with instrument drier (66), sterile adapter (219), motor tenement caps (218), etc.

Turning to FIGS. 15A-15G, single direction rotation lock (284) includes a vertically extending locking surface (283) and a slanted camming surface (285). Additionally, single direction lockout ring (290) includes an annular array of cam teeth (292), each having a locking surface (294) and a slanted camming surface (296). Adjacent cam teeth (292) are arranged such that locking surface (294) of a first cam tooth (292) is directly adjacent to slanted camming surface (296) of the adjacent cam tooth (292). Further adjacent teeth (292) are sufficiently spaced apart in order to define a recessed pocket (298). As shown between FIGS. 15A-15B, single direction rotation lock (284) is dimensioned to fit within recessed pockets (298) in the locked configuration.

Figure 15A:
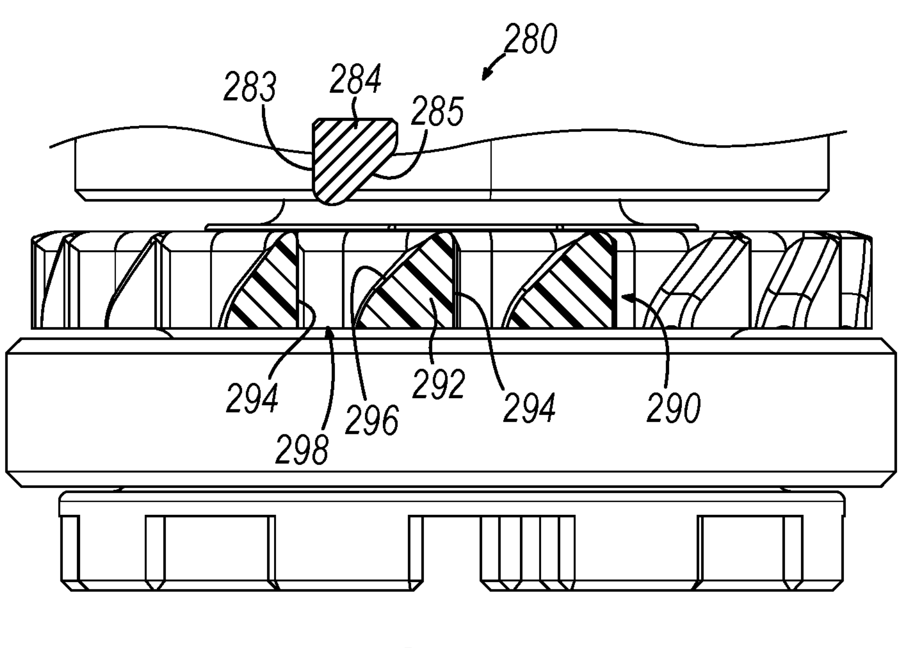
FIG. 15A depicts a cross-sectional view, taken along line 15-15 of FIG. 14A, of the shaft insertion lockout assembly of FIG. 14A in the unlocked configuration.
Figure 15B:
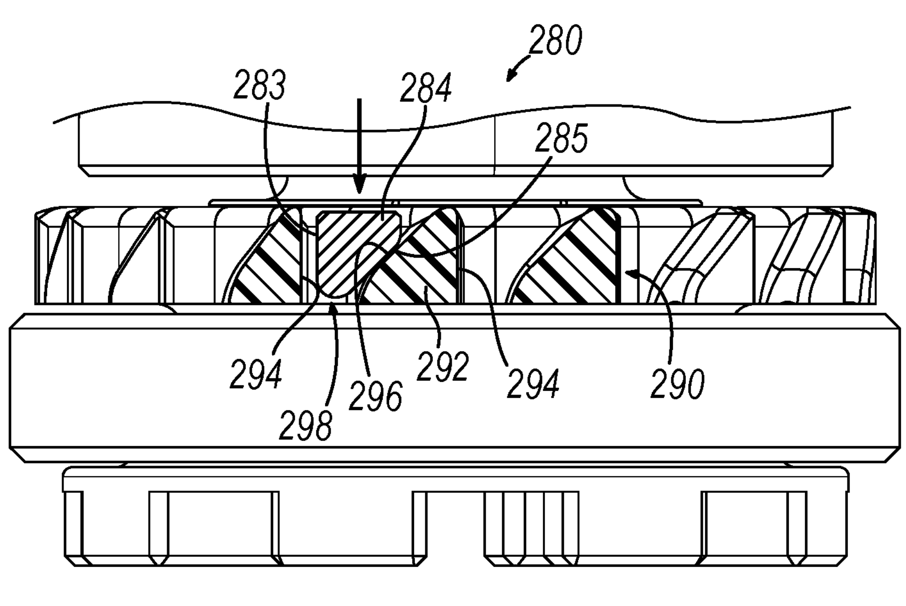
FIG. 15B depicts a cross-sectional view, taken along line 15-15 of FIG. 14A, of the shaft insertion lockout assembly of FIG. 14A in the locked configuration.
Figure 15C:
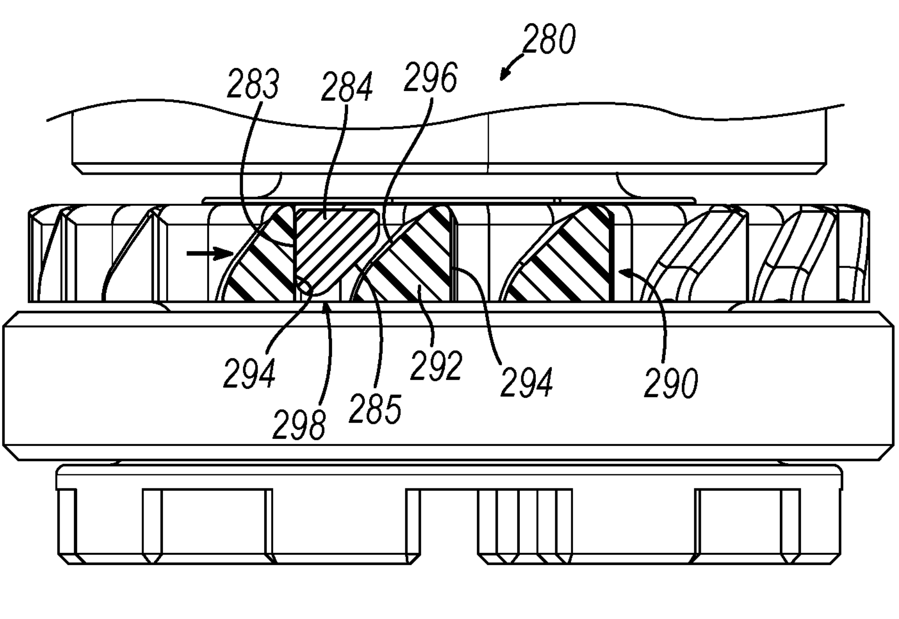
FIG. 15C depicts a cross-sectional view, taken along line 15-15 of FIG. 14A, of the shaft insertion lockout assembly of FIG. 14A in the locked configuration and prevented from rotating in a first angular direction.
Figure 15D:
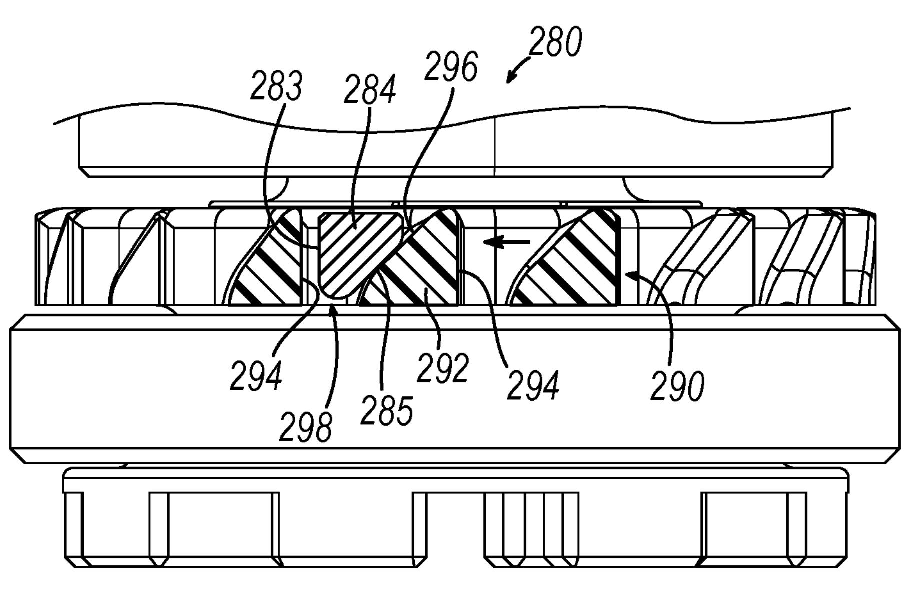
FIG. 15D depicts a cross-sectional view, taken along line 15-15 of FIG. 14A, of the shaft insertion lockout assembly of FIG. 14A in the locked configuration and initially rotating in a second angular direction.
Figure 15E:
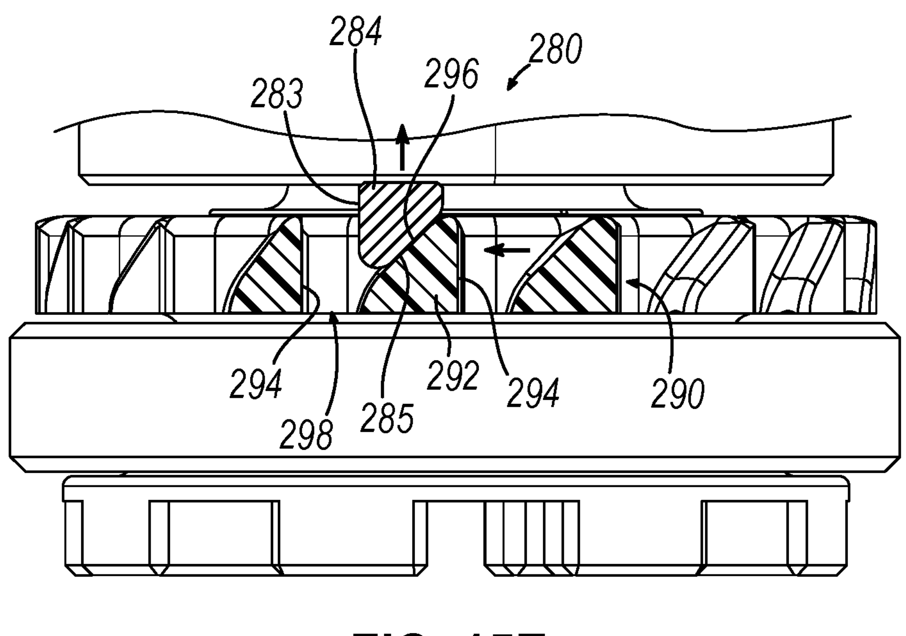
FIG. 15E depicts a cross-sectional view, taken along line 15-15 of FIG. 14A, of the shaft insertion lockout assembly of FIG. 14A in the locked configuration and rotating in the second angular direction such that a rotation lock actuates on top of a camming surface of a lockout ring.
Figure 15F:
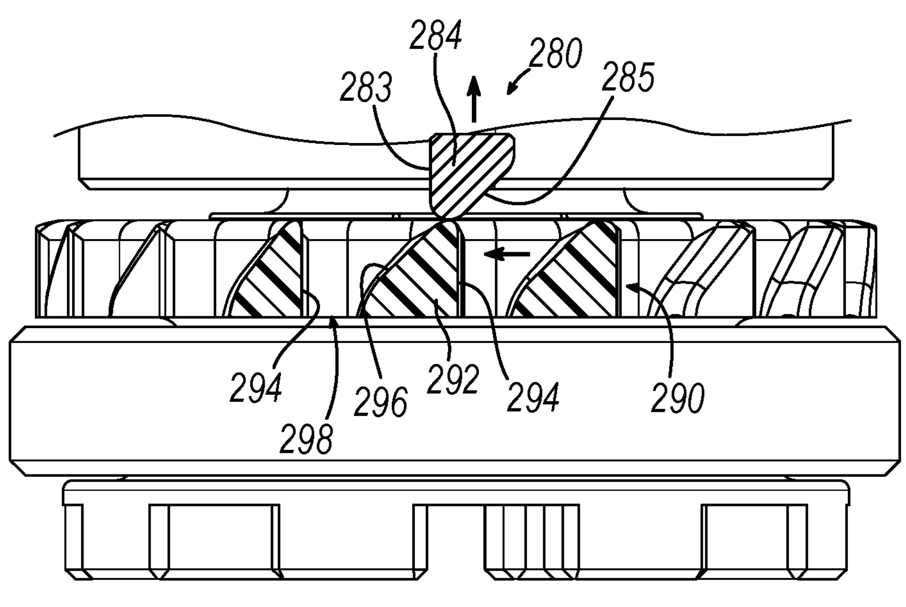
FIG. 15F depicts a cross-sectional view, taken along line 15-15 of FIG. 14A, of the shaft insertion lockout assembly of FIG. 14A in the locked configuration and rotating in the second angular direction such that the rotation lock of FIG. 15E further actuates on top of the camming surface of the lockout ring of FIG. 15E.

As shown in FIG. 15C, if a bailout procedure is completed or instrument (200) is otherwise decoupled from robotic arm (32), a user may accidentally attempt to further insert shaft assembly (114) and end effector (116) within a surgical site, thereby rotating drive input assembly (220) in the direction shown in FIG. 15C. However, with lockout assembly (280) in the locked configuration, locking surfaces (283, 294) engage each other. With biased locking assembly (282) being coupled to chassis assembly (216), engagement between vertical locking surface (283, 294) inhibits further rotational movement of drive input assembly (220) in the direction shown in FIG. 15C.

Figure 15G:
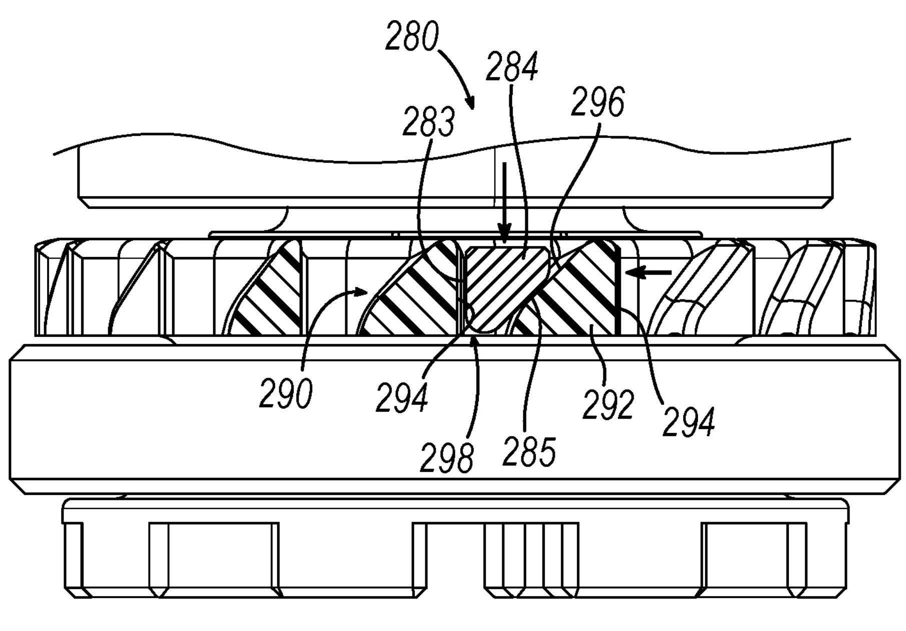
FIG. 15G depicts a cross-sectional view, taken along line 15-15 of FIG. 14A, of the shaft insertion lockout assembly of FIG. 14A in the locked configuration and rotating in the second angular direction such that the rotation lock of FIG. 15E clears the camming surface of the lockout ring of FIG. 15E.

However, as shown between 15D-15G, after a completed bailout procedure, a user may attempt to manually retract shaft assembly (114) and end effector (116) from the surgical site, thereby attempting to rotate drive input assembly (220) in the opposite direction shown in FIG. 15C. With lockout assembly (280) in the locked configuration, camming surfaces (285, 296) engage each other. Engagement between camming surfaces (285, 296) overcomes the biasing force imparted on biased locking assembly (282) such that single direction rotation lock (284) is driven upward until camming surfaces (285, 296) are no longer engaged with each other. Once camming surfaces (285, 296) are no longer engaged with each other, as shown in FIG. 15G, the biased nature of biased locking assembly (282) drives rotation lock (284) into a new recessed pocket (298) defined by adjacent teeth (290). With single direction rotation lock (284) being driven upward and camming surfaces (285, 296) slidingly engaging each other, drive input assembly (220) is allowed to rotate in the direction associated with shaft assembly (114) being proximally retracted.

IV. Illustrative Knife Retraction Bailout Assembly

As mentioned above, knife member (125) may be configured to be driven within jaws (120, 122) between a proximal position (see FIG. 7A) and a distal position (see FIG. 7C) in order to sever tissue. In some instances, a bailout procedure may be required while knife member (125) is actuated distally past the proximal position. In such instances, jaws (120, 122) may be required to be opened after the bailout procedure in order to suitably release grasped tissue. In such instances, it may be desirable to ensure that knife member (125) is suitably retracted prior to opening jaws (120, 122) to release grasped tissue, in order to inhibit any undesirable exposure of knife member (125) to surrounding tissue.

Figure 16:
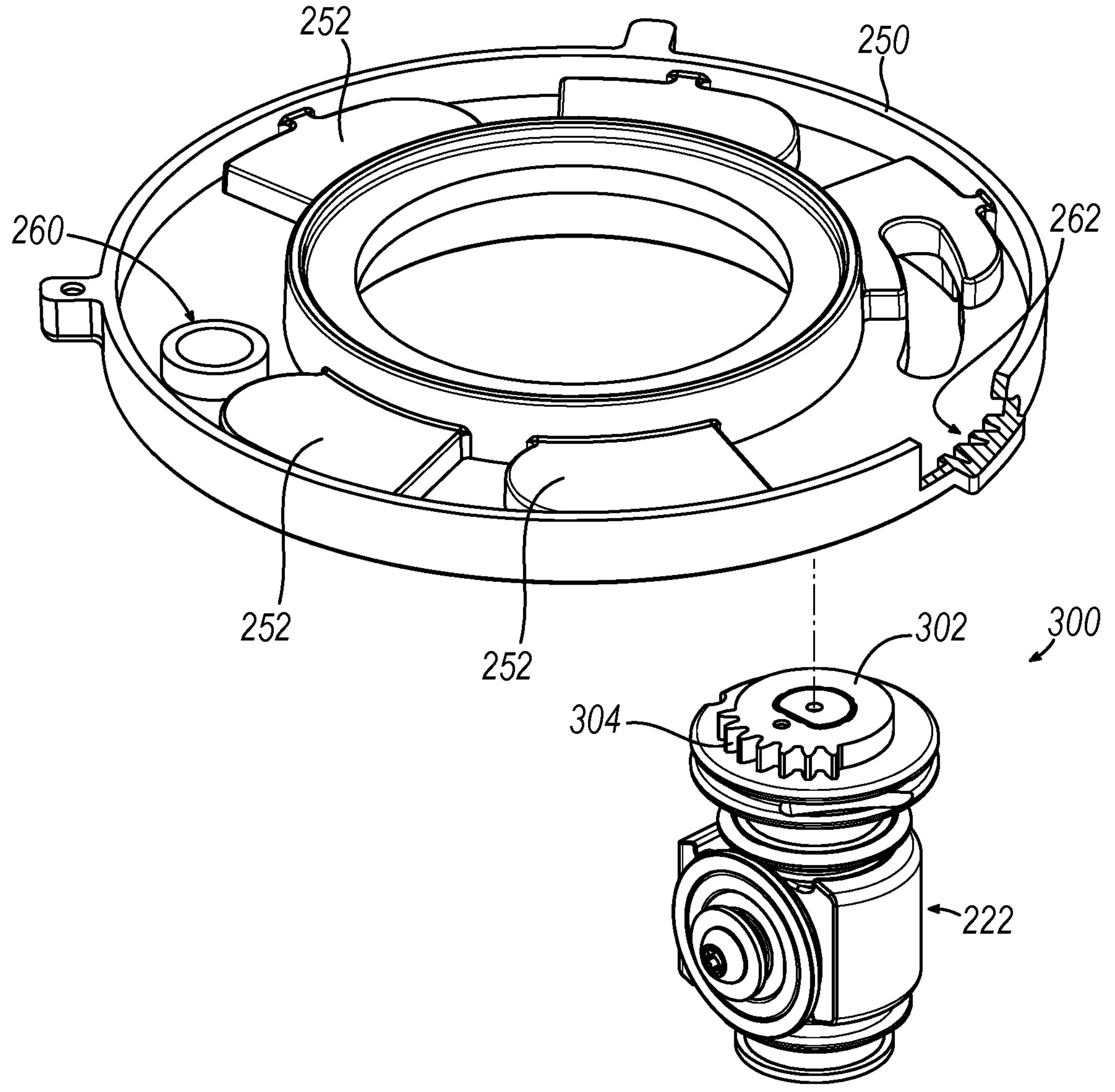
FIG. 16 depicts a perspective view of a knife retraction bailout assembly.

FIG. 16 shows an illustrative knife retraction bailout assembly (300). As will be described in greater detail below, knife retraction bailout assembly (300) is associated with both cam plate (250) of bailout assembly (230) and knife retraction input assembly (222) of instrument base (210) such that if knife member (125) is located distally from its proximal position, knife reaction bailout assembly (300) will automatically retract knife member (125) into the proximal position, during the bailout process.

As mentioned above, in instances where a cable is used to actuate knife member (125) within knife channel (124) between the proximal and distal positions, such a cable may be attached to a first drive input (80) dedicated to distally actuating knife member (125); while the cable may also be attached to a second drive input (80) dedicated to proximally actuating knife member (125). In the current example, instrument (200) includes a knife advancement input assembly (224) and a knife retraction input assembly (222) that may be utilized together to advance and retract knife member (125) in accordance with the description herein.

Knife retraction bailout assembly (300) includes a bailout gear (302) fixed to knife retraction input assembly (222) and a knife retraction sector gear (262) fixed to cam plate (250). Bailout gear (302) is fixed to knife retraction input assembly (222) such that rotation of bailout gear (302) drives a corresponding rotation of knife retraction input assembly (220). Bailout gear (302) includes a knife reaction sector gear (304) configured to selectively engage sector gear (262) of cam plate (250) as cam plate (250) is rotated into the bailout position shown in FIG. 13D.

Figure 17A:
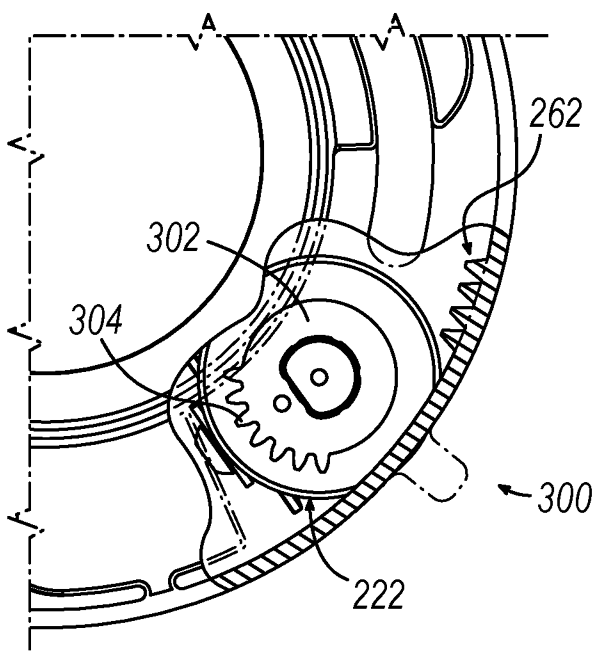
FIG. 17A depicts a top plan view of the knife retraction bailout assembly of FIG. 16 in a pre-bailout position associated with a knife member in a proximal position.
Figure 17B:
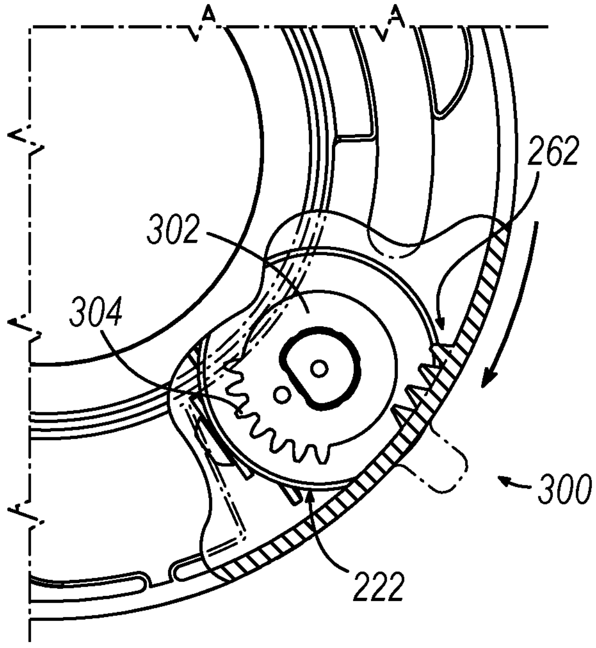
FIG. 17B depicts a top plan view of the knife retraction bailout assembly of FIG. 16 in a bailout position associated with a knife member in a proximal position.

As shown between FIGS. 17A-17B, if knife member (125) is in the proximal position, knife retraction sector gear (304) does not engage sector gear (262) of cam plate (250) a cam plate (250) is rotated into the bailout position shown in FIG. 13D.

Figure 18A:
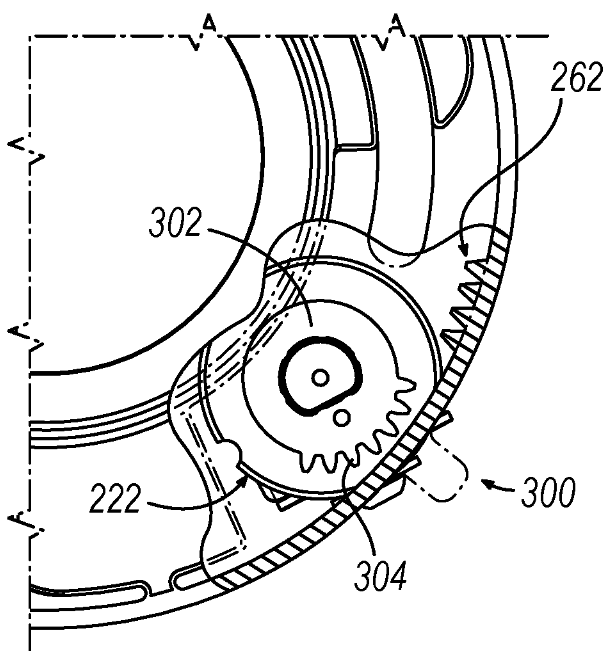
FIG. 18A depicts a top plan view of the knife retraction bailout assembly of FIG. 16 in a pre-bailout position associated with a knife member in a distal position.
Figure 18B:
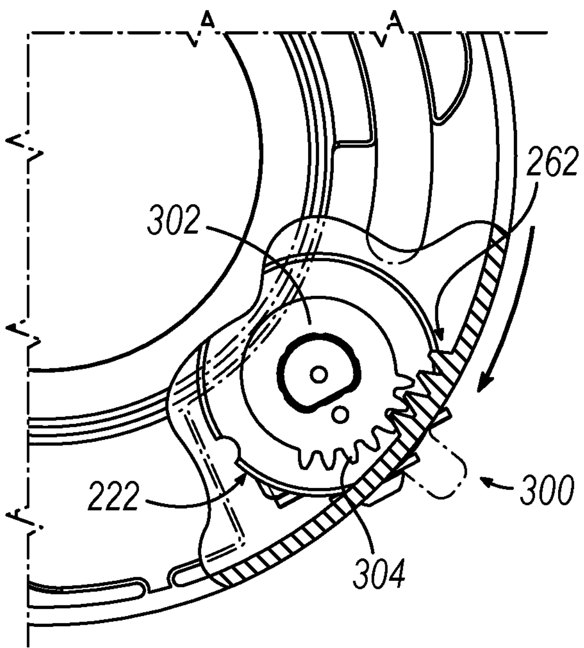
FIG. 18B depicts a top plan view of the knife retraction bailout assembly of FIG. 16 in an intermediary bailout position.
Figure 18C:
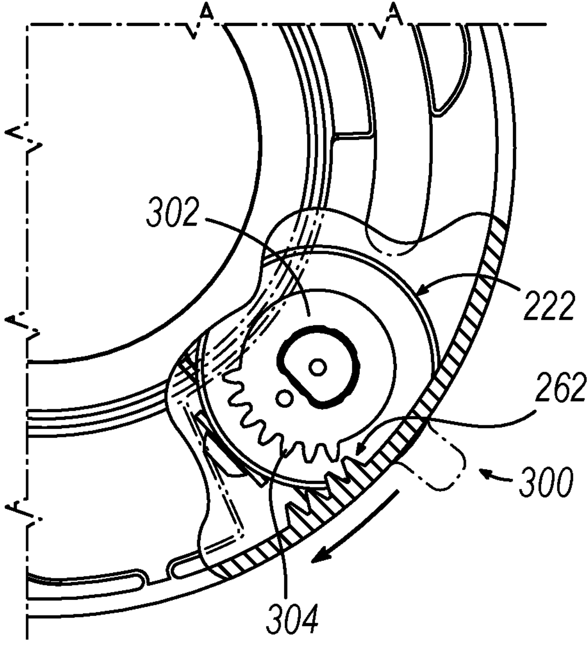
FIG. 18C depicts a top plan view of the knife retraction bailout assembly of FIG. 16 in a bailout position associated with a knife member in a distal position.
Figure 19A:
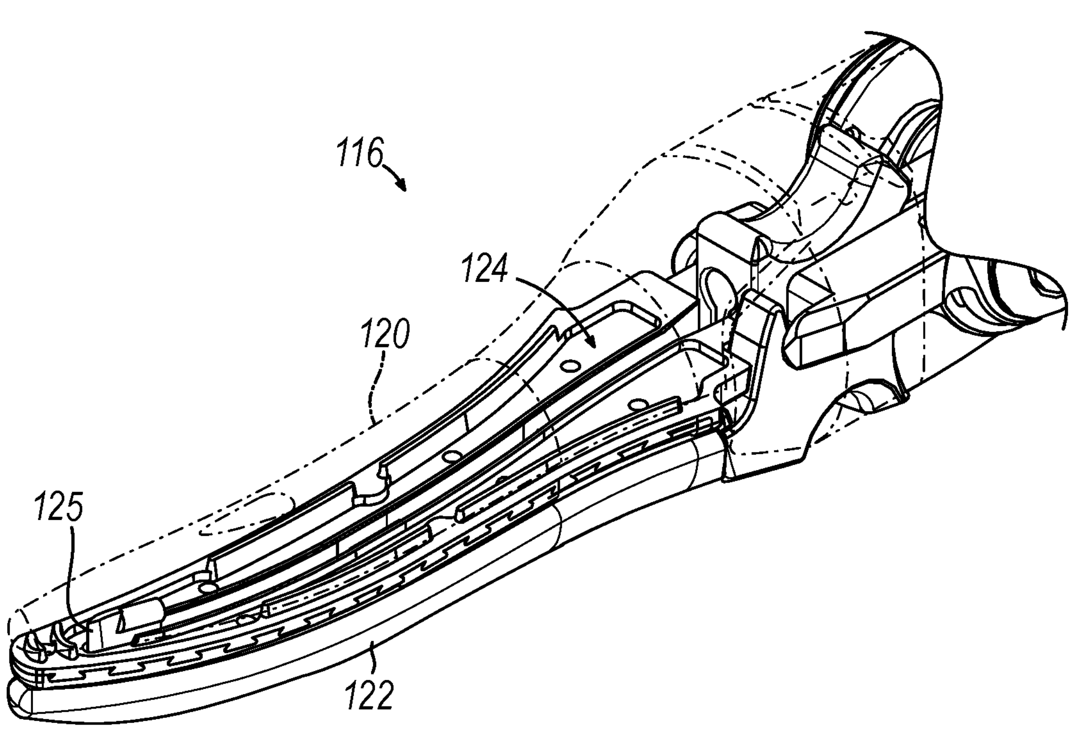
FIG. 19A depicts a perspective view of an end effector coupled with the knife retraction bailout assembly of FIG. 16, with a knife member in the distal position.
Figure 19B:
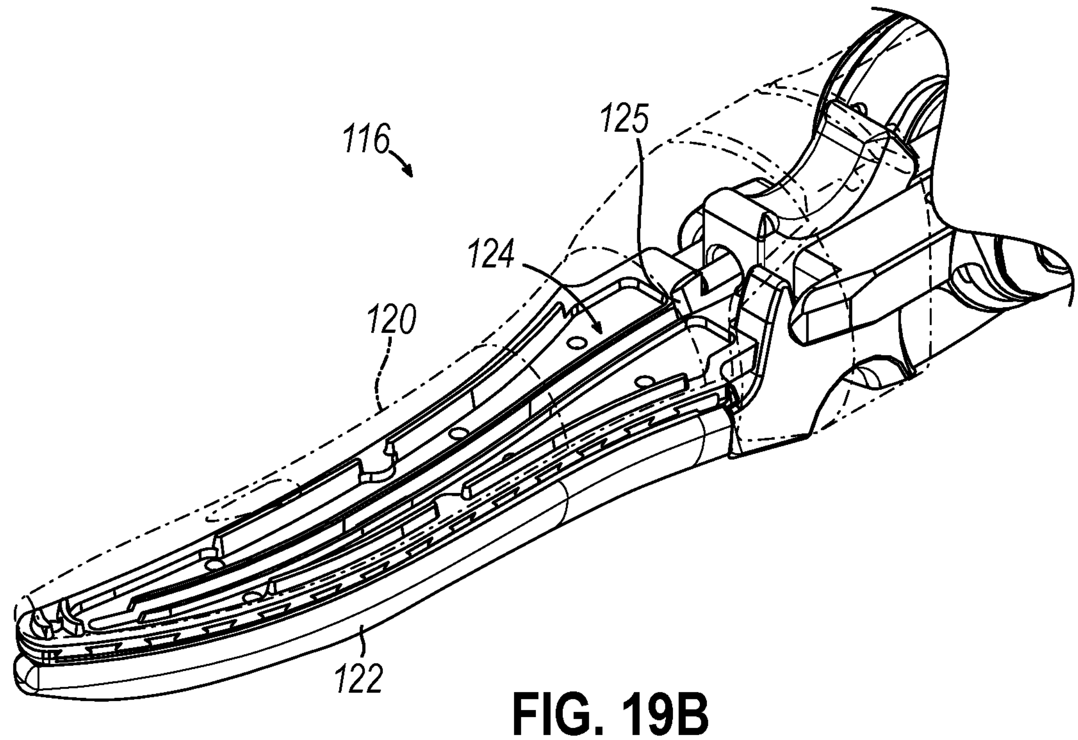
FIG. 19B depicts a perspective view of an end effector coupled with the knife retraction bailout assembly of FIG. 16, with a knife member driven into the proximal position.

However, as shown in FIGS. 18A-18C, if knife member (125) is in a position distal from the proximal position shown in FIG. 17A, knife retraction sector gear (304) is dimensioned to engage complementary sector gear (262) of cam plate (250). Engagement between gears (304, 262) drives rotation of knife retraction input assembly (222) into a direction associated with proximal retraction of knife member (125). Therefore, as shown between FIGS. 19A-19B, if cam plate is rotated into the bailout position while knife member (125) is in a distal position, knife retraction bailout assembly (300) drives rotation of input assembly (222) to thereby automatically return knife member (125) to the proximal position.

V. Illustrative Decoupling Lockout and Shaft Clocking Assembly

While shaft assembly (114) is operatively coupled to instrument base (210), it may be desirable to ensure that shaft assembly (114) is rotationally locked relative to instrument base (210) such that shaft assembly (114) may translate relative to instrument base (210) but not rotate about its own longitudinal axis relative to instrument base (210). Additionally, it may be desirable to prevent proximal housing (212) from decoupling with chassis assembly (216) unless shaft assembly (114) is in a suitably retracted position relative to instrument base (210) or a bailout procedure is performed.

Figure 20A:
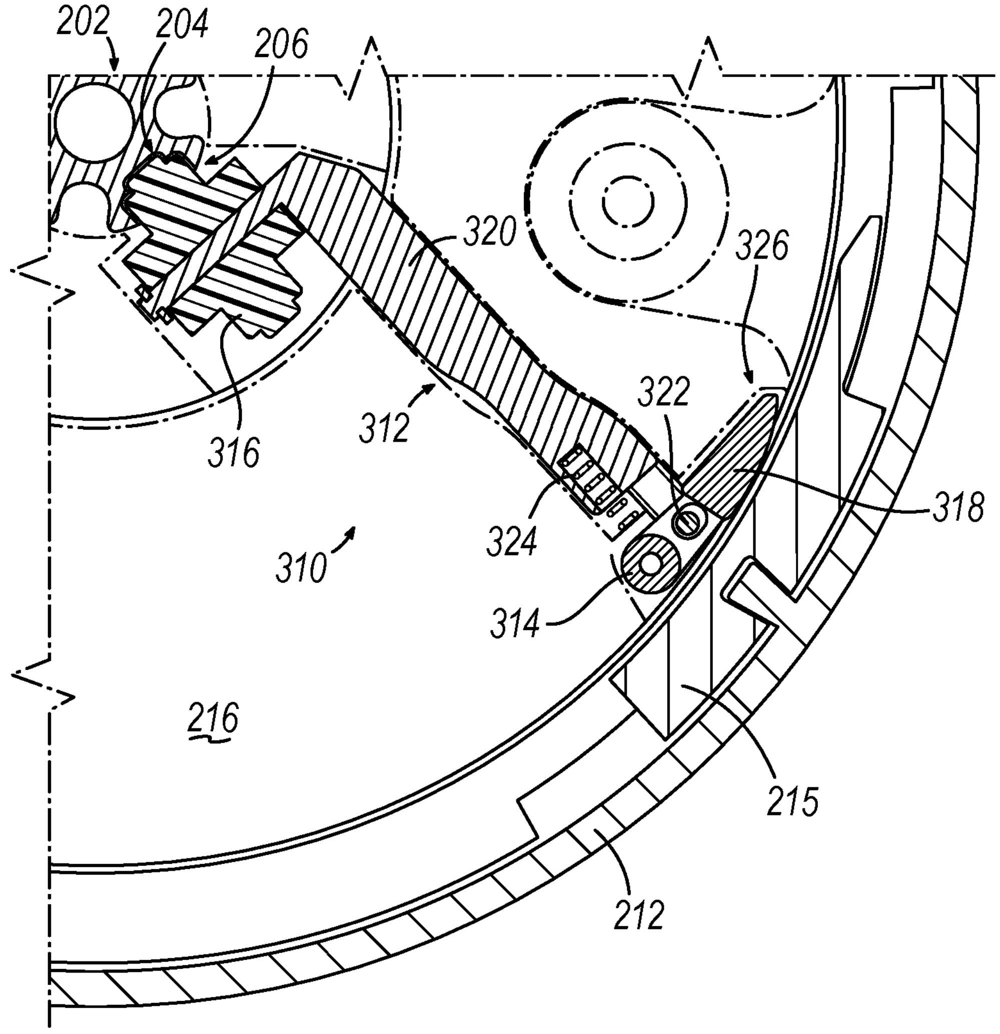
FIG. 20A depicts a cross-sectional view of a decoupling lockout and shaft clocking assembly in an unlocked configuration.
Figure 20B:
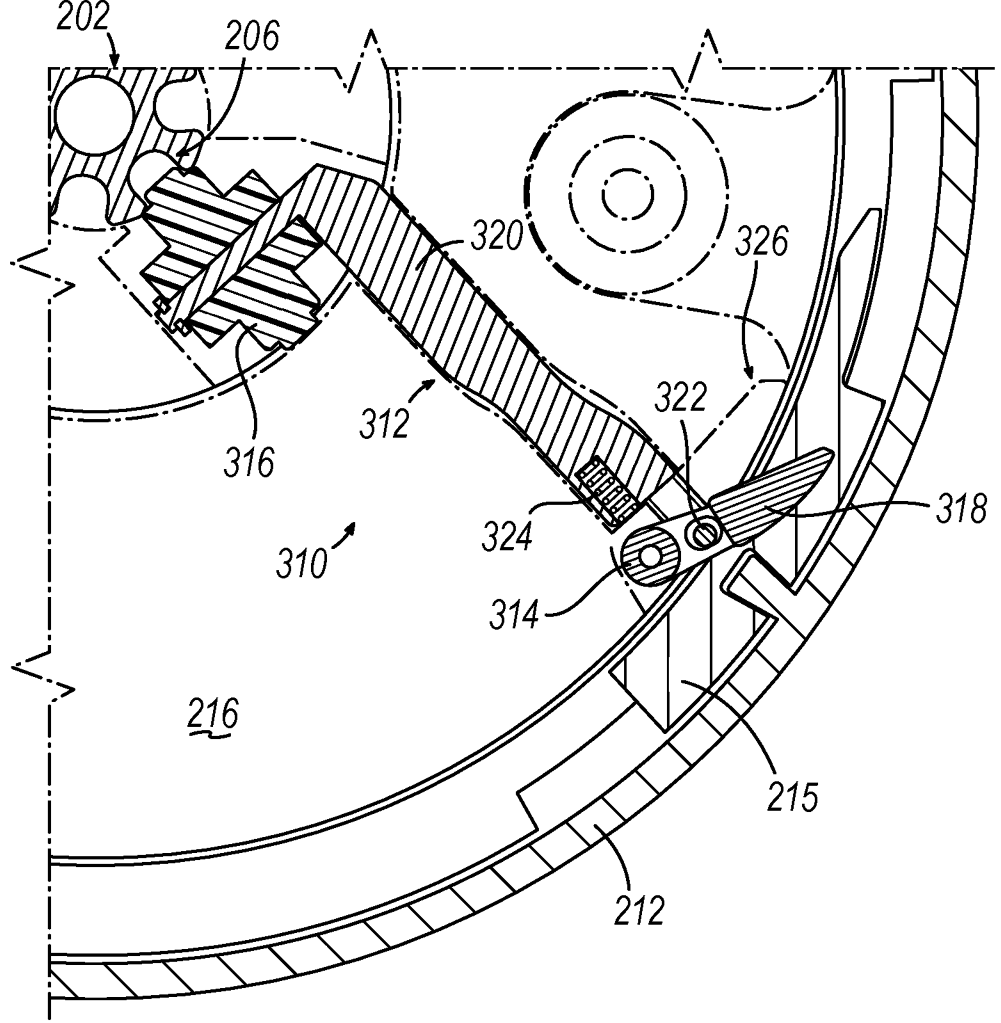
FIG. 20B depicts a cross-sectional view of the decoupling lockout and shaft clocking assembly of FIG. 20A in a locked configuration.
Figure 21:
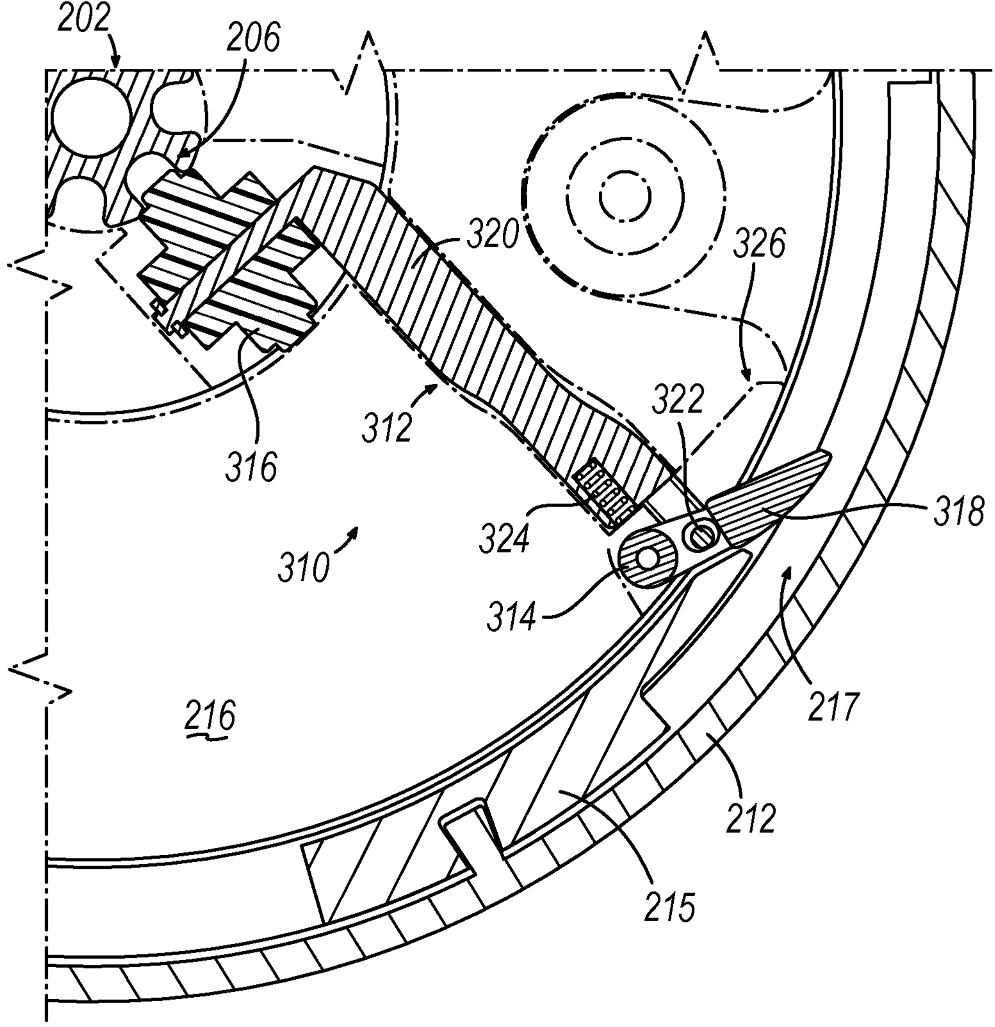
FIG. 21 depicts a cross-sectional view of the decoupling lockout and shaft clocking assembly of FIG. 20A in a bailed out configuration.

FIGS. 20A-21 show an illustrative decoupling lockout and shaft clocking assembly (310). As will be described in greater detail below, assembly (310) rotationally locks shaft assembly (114) relative to instrument base (210), and also prevents proximal housing (212) from decoupling with chassis assembly (216) unless specified conditions are satisfied.

Assembly (310) includes a saddle channel (312) defined by chassis assembly (216), a chassis pivot pin (314), a clocking wheel (316), a pivot locking link (318), a translating saddle (320), a saddle driving pin (322), a bias spring (324), and a locking link recess housing (326) defined by chassis assembly (216). Translating saddle (320) is slidably disposed within saddle channel (312) along a path defined by saddle channel (312). Translating saddle (320) is biased via spring (324) inwardly toward proximal portion (202) of shaft assembly (214). Clocking wheel (316) is attached to saddle (320) and is also slidably disposed within a longitudinally extending flute (206) defined by proximal portion (202) of shaft assembly (114). Clocking wheel (316) engages flute (206) to rotationally fix shaft assembly (114). Clocking wheel (316) is also configured to roll along the length of flute (206) as shaft assembly (114) is advanced and retracted in accordance with the description herein.

As shown in FIG. 20A, flute (206) also defines a discrete detent (204) located at a distal end of proximal portion (202). Detent (204) is deeper relative to the remaining portion of flute (206) such that when clocking wheel (316) is within detent, clocking wheel (316) and saddle (320) are biased via spring (324) closer to the central longitudinal axis of shaft assembly (214). Detent (204) is located on flute (206) such that clocking wheel (316) rests within detent (204) while shaft assembly (114) is in the fully retracted position.

Locking link (318) is pivotably coupled to chassis assembly (216) via chassis pivot pin (314). Additionally, locking link (318) is attached to saddle driving pin (322). Saddle driving pin (322) is fixed to saddle (320) such that translation of saddle (320) within saddle channel (312) pivots locking link (318) about chassis pin (314). Therefore, the position of saddle (320) within saddle channel (312) determines the pivotal position of link (318). Locking link (318) is configured to pivot from an unlocked configuration (see FIG. 20A), where link (318) is housed within recessed housing (326), into a locked configuration (see FIG. 20B), where link (318) extends from recessed housing (326) and is interposed between a locking ledge (215) associated with proximal housing (212) and chassis assembly (216). While link (318) is interposed between locking ledge (215) and chassis assembly (216), proximal housing (212) is prevented from decoupling with chassis assembly (216).

As shown in FIG. 20A, if shaft assembly (114) is in the retracted position, clocking wheel (316) is driven into detent (204) via saddle (320) and spring (324) in accordance with the description herein. Additionally, saddle driving pin (322) drives locking link (322) into recess (326) such that locking link (318) is not interposed between lockout ledge (215) and chassis assembly (216). Therefore, while shaft assembly (114) is in the retracted position, detent (204) allows for saddle (320) to drive lockout link (318) into an unlocked configuration such that proximal housing (215) may decouple from chassis assembly (216).

As shown in FIG. 20B, if shaft assembly (114) is advanced distally from the retracted position, clocking wheel (316) is driven out of detent (204) and within a shallow portion of flute (206). Therefore, the shallow portion of flute (206) drives saddle (320) further away from proximal portion (202) of shaft assembly (114) if shaft assembly (114) is in a distal position relative to instrument base (210). Driving pin (322) of saddle (320) therefore pivots link (318) into a locked configuration such that link (318) is interposed between chassis assembly (216) and lockout ledge (215) of proximal housing (212). With link (318) being interposed between chassis assembly (216) and lockout ledge (215) proximal housing (212) is prevented from decoupling from chassis assembly (216). Therefore, if shaft assembly (114) is advanced out of the retracted position, assembly (310) inhibits proximal housing (212) and chassis assembly (216) from decoupling.

However, as shown in FIG. 21, if proximal housing (212) is rotated via the bailout procedure described above, proximal housing (212) defines a bailout cutout (217) such that link (318) is no longer interposed between proximal housing (212) and chassis assembly (216). Therefore, if a bailout procedure is performed, proximal housing (212) is removable from chassis assembly (216), even though clocking wheel (316) is located within a shallow portion of flute (206).

Additionally, it should be understood that clocking wheel (316) keeps shaft assembly (114) rotationally fixed relative to instrument base (210) while shaft assembly (114) is suitably attached to instrument base (210). Therefore, assembly (310) provides a space saving measure to both rotationally fix shaft assembly (114) relative to instrument base (210); as well as inhibit decoupling of proximal housing (212) from chassis assembly (216) unless shaft assembly (114) is in the fully retracted position or a bailout procedure has been performed.

In some instances, a pivoting link (318) may be omitted such that saddle (320) performs the lockout functionality.

V. Illustrative Dual Torque Spring Knife Retraction Assembly

As mentioned above, in instances where a cable is used to actuate knife member (125) within knife channel (124) between the proximal and distal positions, such a cable may be attached to both a knife advancement input assembly (224) dedicated to distally driving knife member (125) and a knife retraction input assembly (222) dedicated to proximally driving knife member (125). In some instances, for suitable reasons as would be apparent to one skilled in the art in view of the teachings herein, it may be desirable to proximally bias knife member (125) in order to help urge proximal retraction of knife member (125). However, having a single torque spring associated with proximal retraction of knife member (125) may lead to an undesirable increase in torque as input assemblies (222, 224) are rotated in order to fire knife member (125) in accordance with the description herein. Therefore, it may be desirable to use two torque springs that are set to apply torque in opposite directions in order to apply a linear retraction force on knife member (125), even as both torque springs are angularly displaced due to firing of knife member (125).

Figure 22:
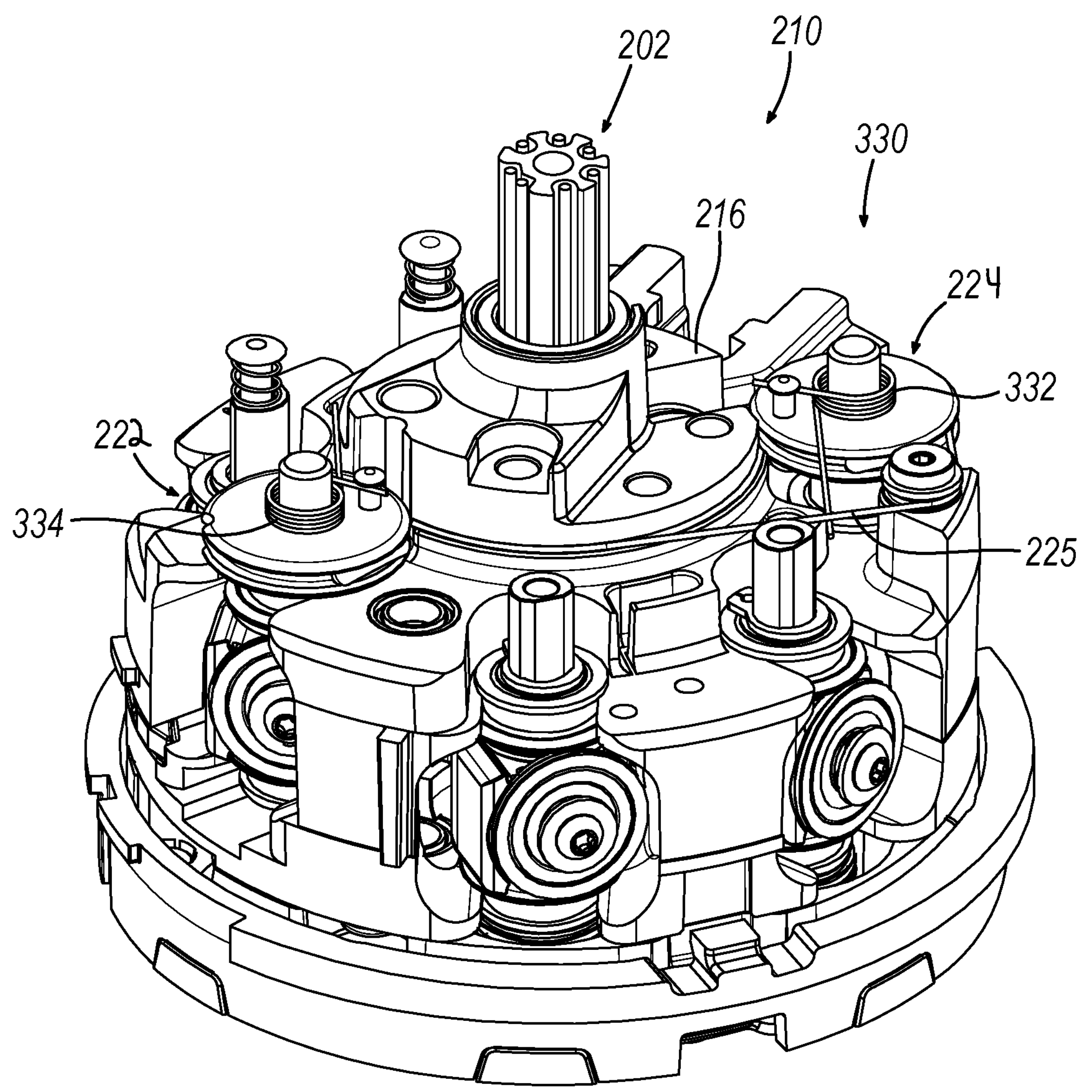
FIG. 22 depicts a perspective view of a dual torque spring knife retraction assembly.
Figure 23:
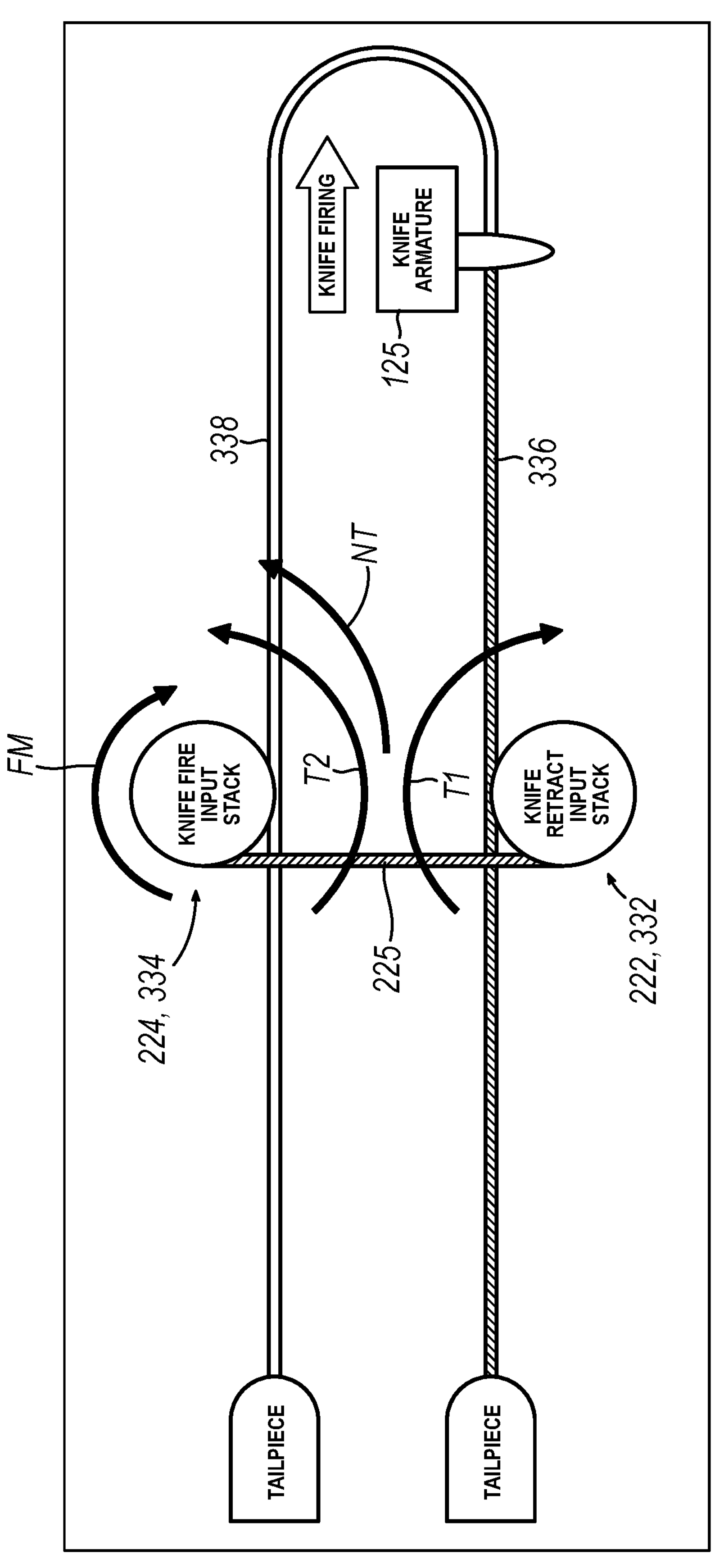
FIG. 23 depicts a schematic view of the dual torque spring knife retraction assembly of FIG. 22.

FIGS. 22-23 show an illustrative dual torque spring knife reaction assembly (330) that includes a first torsion spring (332) associated with knife retraction input assembly (222), and a second torsion spring (332) associated with knife advancement input assembly (224). Knife member (125) is fixed to both retraction cable (336) and advancement cable (338), which are wound around their respective input assembly (222, 224). A coupling cable (225) is also attached to both input assemblies (222, 224).

Figure 24:
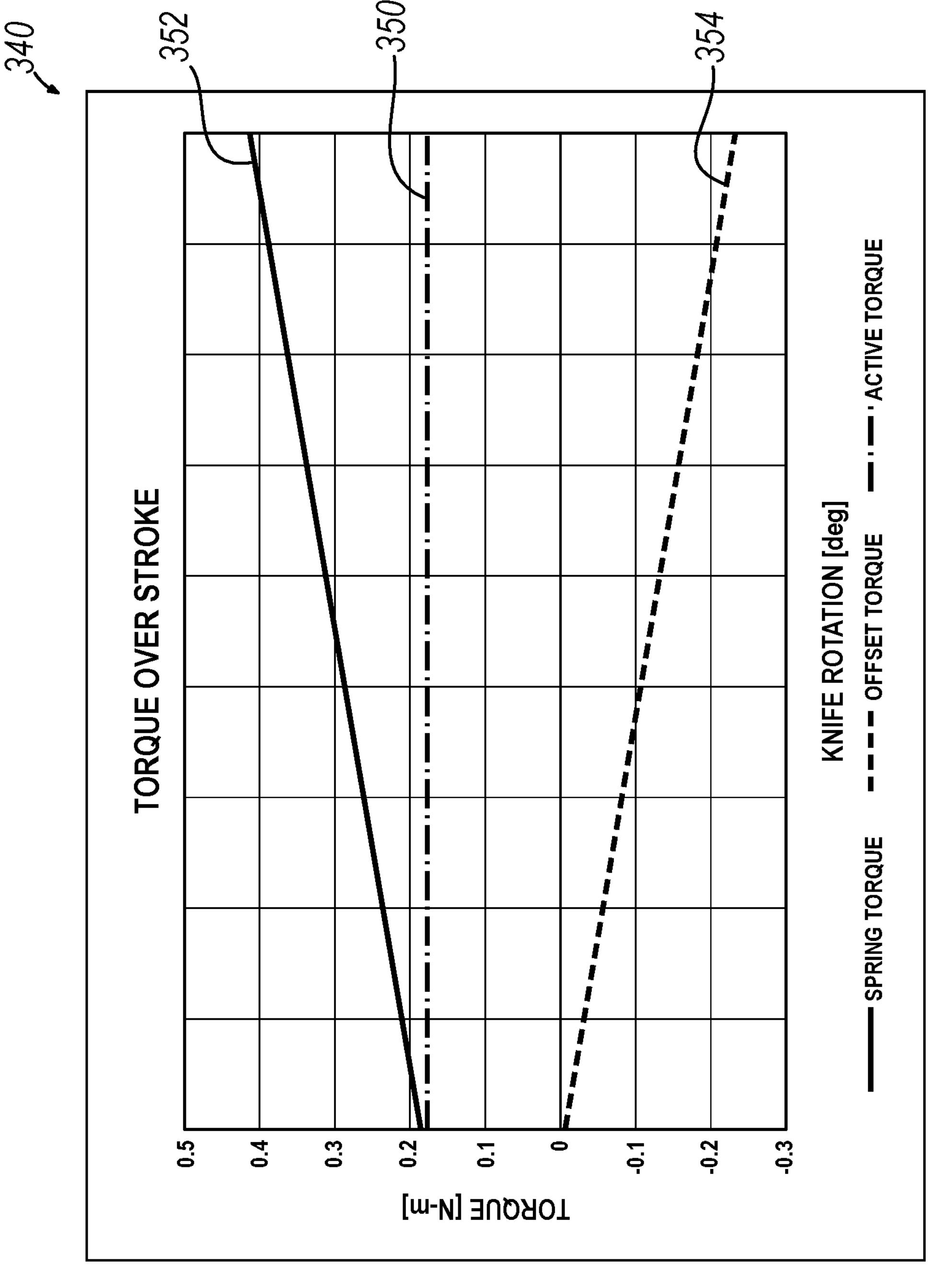
FIG. 24 depicts a graph of the torque generated by the dual torque spring knife retraction assembly of FIG. 22 over a firing stroke.

FIG. 24 shows a graph of the torque over the firing stroke, with the spring torque (352) associated with retracting knife member (125), the active torque (354) associated with second torsion spring (334), and the offset net torque (350) imparted on the system during the firing stroke.

First torque spring (332) is wound to impart a retraction force on knife member (125) as knife member (125) is in the pre-fired position; while second torque spring (334) is wound to impart little or no advancement force on knife member (125) as knife member (125) is in the pre-fired position. As a firing sequence starts, first torque spring (332) imparts an increasing first torque (T1), while second torque spring (334) imparts a second torque (T2) in the opposite direction. Each torque spring (332, 334) may have substantially similar spring constants, such that as knife member (125) is fired along its stroke, as visualized in FIG. 24, the proximally presented net torque (NT, 350) remains substantially constant.

VI. Illustrative Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) an end effector configured to manipulate tissue; (b) a shaft assembly extending proximally from the end effector; (c) an instrument base, wherein a portion of the shaft assembly located proximally relative to the end effector extending through the instrument base, wherein the instrument base comprises at least one input assembly configured to operatively engage an output assembly of a robotic arm, wherein the at least one input assembly is configured to actuate to thereby control movement of the end effector, wherein the output assembly for the robotic arm is configured to drive actuation of the at least one input assembly; and (d) a bailout assembly, wherein the bailout assembly comprises: (i) an actuating body configured to actuate relative to the instrument base from a pre-bailout position, an engaged position, and a bailout position, and (ii) a driving assembly configured actuate from a first position toward a second position to drive the output assembly of the robotic arm out of engagement with the at least one input assembly of the instrument base in response to the actuating body actuating from the engaged position into the bailout position, wherein the driving assembly is configured to remain in the first position while the actuating body is in the pre-bailout position.

Example 2

The apparatus of any one or more of the preceding Examples, wherein the driving assembly comprises a cam plate and a pogo pin.

Example 3

The apparatus of any one or more of the preceding Examples, wherein the cam plate is configured to drive the pogo pin in response to actuating from the first position toward the second position.

Example 4

The apparatus of any one or more of the preceding Examples, further comprising a bailout engagement feature slidably attached to the cam plate.

Example 5

The apparatus of any one or more of the preceding Examples, wherein the bailout engagement feature is configured to couple with the actuating body in response to the actuating body reaching the engaged position.

Example 6

The apparatus of any one or more of the preceding Examples, wherein the bailout engagement feature is biased toward the actuating body.

Example 7

The apparatus of any one or more of the preceding Examples, wherein the end effector comprises a knife member configured to actuate between a pre-fired position and a fired position.

Example 8

The apparatus of any one or more of the preceding Examples, further comprising an automatic knife retraction assembly configured to drive the knife member toward the pre-fired position in response to the driving assembly actuating from a first position toward a second position.

Example 9

The apparatus of any one or more of the preceding Examples, wherein the automatic knife retraction assembly comprises a first sector gear associated with the driving assembly.

Example 10

The apparatus of any one or more of the preceding Examples, wherein the automatic knife retraction assembly comprises a second sector gear associated with the at least one input assembly.

Example 11

The apparatus of any one or more of the preceding Examples, further comprising a shaft insertion lockout assembly configured to inhibit distal movement of the shaft assembly once the driving assembly reaches the second position.

Example 12

The apparatus of any one or more of the preceding Examples, wherein the shaft insertion lockout assembly comprise a biased locking body slidably coupled to a chassis assembly of the instrument base.

Example 13

The apparatus of any one or more of the preceding Examples, wherein the shaft insertion locking assembly comprise an annular array of locking teeth fixed to a first input assembly of the at least one input assembly.

Example 14

The apparatus of any one or more of the preceding Examples, further comprising a shaft clocking assembly configured to rotational fix the shaft assembly relative to the instrument base about a longitudinal axis of the shaft assembly.

Example 15

The apparatus of any one or more of the preceding Examples, wherein the shaft clocking assembly is configured to inhibit disassembly of the instrument base unless the shaft assembly is in a predetermined retracted position or the driving assembly is in the second position.

Example 16

An apparatus, comprising: (a) an end effector configured to manipulate tissue; (b) a shaft assembly extending proximally from the end effector; (c) an instrument base, wherein a portion of the shaft assembly located proximally relative to the end effector extending through the instrument base, wherein the instrument base comprises at least one input assembly configured to operatively engage an output assembly of a robotic arm, wherein the at least one input assembly is configured to actuate to thereby control movement of the end effector, wherein the output assembly for the robotic arm is configured to drive actuation of the at least one input assembly; and (d) a two-stage bailout assembly configured to drive the output assembly of the robotic arm out of engagement with the at least one input assembly of the instrument base, wherein the two-stage bailout assembly comprises a user-input feature configured to actuate through a first range of motion to render the two-stage bailout assembly operable, wherein the user-input feature is configured to actuate through a second range of motion to drive the output assembly of the robotic arm out of engagement with the at least one input assembly of the instrument base.

Example 17

The apparatus of any one or more of the preceding Examples, wherein the end effector comprises a pair of jaws.

Example 18

The apparatus of any one or more of the preceding Examples, wherein the two-stage bailout assembly is associated with the instrument base.

Example 19

The apparatus of any one or more of the preceding Examples, wherein the at least one input assembly comprises a pair of input assemblies configured to drive a knife member of the end effector.

Example 20

An apparatus, comprising: (a) an end effector configured to manipulate tissue; (b) a shaft assembly extending proximally from the end effector; (c) an instrument base slidably housing the shaft assembly, wherein the instrument base comprises at least one input assembly configured to operatively engage an output assembly of a robotic arm, wherein the at least one input assembly is configured to actuate to thereby control movement of the end effector, wherein the output assembly for the robotic arm is configured to drive actuation of the at least one input assembly; and (d) a two-stage bailout assembly configured to remain inoperable until a first condition is satisfied, wherein the two-stage bailout assembly is configured to drive the output assembly of the robotic arm out of engagement with the at least one input assembly of the instrument base in response to a second condition being satisfied after the first condition is satisfied.

VII. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus, comprising:

(a) an end effector configured to manipulate tissue;

(b) a shaft assembly extending proximally from the end effector;

(c) an instrument base, wherein a portion of the shaft assembly located proximally relative to the end effector extending through the instrument base, wherein the instrument base comprises at least one input assembly configured to operatively engage an output assembly of a robotic arm, wherein the at least one input assembly is configured to actuate to thereby control movement of the end effector, wherein the output assembly for the robotic arm is configured to drive actuation of the at least one input assembly; and (d) a bailout assembly, wherein the bailout assembly comprises:

(i) an actuating body configured to acuate relative to the instrument base from a pre-bailout position, an engaged position, and a bailout position, and (ii) a driving assembly configured actuate from a first position toward a second position to drive the output assembly of the robotic arm out of engagement with the at least one input assembly of the instrument base in response to the actuating body actuating from the engaged position into the bailout position, wherein the driving assembly is configured to remain in the first position while the actuating body is in the pre-bailout position, wherein the actuating body is configured to actuate from the pre-bailout position into the engaged position while the output assembly of the robotic arm and the at least one input assembly of the instrument base remain operatively engaged with each other.

2. The apparatus of claim 1, wherein the driving assembly comprises a cam plate and a pogo pin.

3. The apparatus of claim 2, wherein the cam plate is configured to drive the pogo pin in response to actuating from the first position toward the second position.

4. The apparatus of claim 3, further comprising a bailout engagement feature slidably attached to the cam plate.

5. The apparatus of claim 4, wherein the bailout engagement feature is configured to couple with the actuating body in response to the actuating body reaching the engaged position.

6. The apparatus of claim 5, wherein the bailout engagement feature is biased toward the actuating body.

7. The apparatus of claim 1, wherein the end effector comprises a knife member configured to acuate between a pre-fired position and a fired position.

8. The apparatus of claim 7, further comprising an automatic knife retraction assembly configured to drive the knife member toward the pre-fired position in response to the driving assembly actuating from a first position toward a second position.

9. The apparatus of claim 8, wherein the automatic knife retraction assembly comprises a first sector gear associated with the driving assembly.

10. The apparatus of claim 9, wherein the automatic knife retraction assembly comprises a second sector gear associated with the at least one input assembly.

11. The apparatus of claim 1, further comprising a shaft insertion lockout assembly configured to inhibit distal movement of the shaft assembly once the driving assembly reaches the second position.

12. The apparatus of claim 11, wherein the shaft insertion lockout assembly comprise a biased locking body slidably coupled to a chassis assembly of the instrument base.

13. The apparatus of claim 12, wherein the shaft insertion locking assembly comprise an annular array of locking teeth fixed to a first input assembly of the at least one input assembly.

14. The apparatus of claim 1, further comprising a shaft clocking assembly configured to rotational fix the shaft assembly relative to the instrument base about a longitudinal axis of the shaft assembly.

15. The apparatus of claim 14, wherein the shaft clocking assembly is configured to inhibit disassembly of the instrument base unless the shaft assembly is in a predetermined retracted position or the driving assembly is in the second position.

16. An apparatus, comprising:

(a) an end effector configured to manipulate tissue;

(b) a shaft assembly extending proximally from the end effector;

(c) an instrument base, wherein a portion of the shaft assembly located proximally relative to the end effector extending through the instrument base, wherein the instrument base comprises at least one input assembly configured to operatively engage an output assembly of a robotic arm, wherein the at least one input assembly is configured to actuate to thereby control movement of the end effector, wherein the output assembly for the robotic arm is configured to drive actuation of the at least one input assembly; and (d) a two-stage bailout assembly configured to drive the output assembly of the robotic arm out of engagement with the at least one input assembly of the instrument base, wherein the two-stage bailout assembly comprises a user-input feature configured to actuate through a first range of motion in a first direction to render the two-stage bailout assembly operable, wherein the user-input feature is configured to actuate through a second range of motion in a second direction to drive the output assembly of the robotic arm out of engagement with the at least one input assembly of the instrument base, wherein the first direction of the first range of motion and the second direction of the second range of motion are different from each other.

17. The apparatus of claim 16, wherein the end effector comprises a pair of jaws.

18. The apparatus of claim 16, wherein the two-stage bailout assembly is associated with the instrument base.

19. The apparatus of claim 16, wherein the at least one input assembly comprises a pair of input assemblies configured to drive a knife member of the end effector.

20. An apparatus, comprising:

(a) an end effector configured to manipulate tissue;

(b) a shaft assembly extending proximally from the end effector;

(c) an instrument base slidably housing the shaft assembly, wherein the instrument base comprises at least one input assembly configured to operatively engage an output assembly of a robotic arm, wherein the at least one input assembly is configured to actuate to thereby control movement of the end effector, wherein the output assembly for the robotic arm is configured to drive actuation of the at least one input assembly; and (d) a two-stage bailout assembly configured to remain inoperable until a first condition is satisfied such that the output assembly of the robotic arm and the at least one input assembly of the instrument base remain engaged with each other both prior to, and after, the first condition is satisfied, wherein the two-stage bailout assembly is configured to drive the output assembly of the robotic arm out of engagement with the at least one input assembly of the instrument base in response to a second condition being satisfied after the first condition is satisfied.

* * * * *